(12) United States Patent  (10) Patent No.: US 7,501,427 B2
Wallace et al.  (45) Date of Patent: Mar. 10, 2009

(54) QUINAZOLINE ANALOGS AS RECEPTOR TYROSINE KINASE INHIBITORS

(75) Inventors: Eli Wallace, Lyons, CO (US); George Topalov, Superior, CO (US); Joseph Lyssikatos, Superior, CO (US); Alexandre Buckmelter, Superior, CO (US); Qian Zhao, Superior, CO (US)

(73) Assignee: Array BioPharma, Inc., Boulder, CO (US)

( * ) Notice: Subject to any disclaimer, the term of this patent is extended or adjusted under 35 U.S.C. 154(b) by 695 days.

(21) Appl. No.: 10/642,440

(22) Filed: Aug. 14, 2003

(65) Prior Publication Data

US 2005/0101616 A1 May 12, 2005

(51) Int. Cl.
*A01N 43/54* (2006.01)
*A61K 31/517* (2006.01)
*C07D 239/00* (2006.01)
*C07D 239/70* (2006.01)
*C07D 471/00* (2006.01)
*C07D 487/00* (2006.01)

(52) U.S. Cl. .................. 514/266.1; 544/245

(58) Field of Classification Search ............. 514/234.5, 514/266.2, 266.3, 266.4, 235.2, 311, 312, 514/313; 544/116, 283, 284, 293, 230; 546/134, 546/135, 159
See application file for complete search history.

(56) References Cited

U.S. PATENT DOCUMENTS

| | | | |
|---|---|---|---|
| 2,583,774 A * | 1/1952 | Hoffman | 546/288 |
| 3,890,319 A * | 6/1975 | Danielewicz et al. | 544/284 |
| 5,112,817 A | 5/1992 | Fukazawa et al. | |
| 5,204,348 A | 4/1993 | Fukazawa et al. | |
| 5,405,843 A | 4/1995 | Fukazawa et al. | |
| 5,502,187 A | 3/1996 | Ayer et al. | |
| 5,821,246 A | 10/1998 | Brown | |
| 5,955,464 A | 9/1999 | Barker | |
| 6,017,922 A * | 1/2000 | Stogniew et al. | 514/266.4 |
| 6,127,374 A | 10/2000 | Bridges | |
| 6,169,091 B1 | 1/2001 | Cockerill et al. | |
| 6,184,225 B1 | 2/2001 | Thomas et al. | |

(Continued)

FOREIGN PATENT DOCUMENTS

WO    WO 96/09294    3/1996

(Continued)

OTHER PUBLICATIONS

Shen et al. European Journal of Medicinal Chemistry, 2007, 42, 81-86.*

(Continued)

*Primary Examiner*—James O Wilson
*Assistant Examiner*—Noble Jarrell
(74) *Attorney, Agent, or Firm*—John R. Moore; McDermott Will & Emery LLP

(57) ABSTRACT

This invention concerns quinazoline analogs of Formula I:

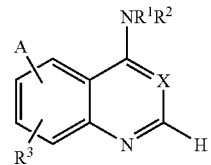

where an A group is bonded to at least one of the carbons at the 5, 6, 7 or 8 position of the bicyclic ring, and the ring is substituted by up to three independent $R^3$ groups. The invention also includes methods of using these compounds as type I receptor tyrosine kinase inhibitors and for the treatment of hyperproliferative diseases such as cancer.

37 Claims, 5 Drawing Sheets

(20)

(14)

(21)

U.S. PATENT DOCUMENTS

| | | | |
|---|---|---|---|
| 6,225,318 | B1 | 5/2001 | Sobolov-Jaynes et al. |
| 6,344,459 | B1 | 2/2002 | Bridges et al. |
| 6,391,874 | B1 | 5/2002 | Cockerill et al. |
| 6,399,602 | B1 | 6/2002 | Barker et al. |
| 6,602,863 | B1 | 8/2003 | Bridges et al. |
| 6,800,605 | B1 | 10/2004 | Friends et al. |
| 6,828,320 | B2 | 12/2004 | Cockerill et al. |
| 6,897,214 | B2 | 5/2005 | Barker et al. |
| 7,081,461 | B1 | 7/2006 | Mortlock et al. |
| 7,109,164 | B2 | 9/2006 | Friends et al. |
| 2002/0042409 | A1 | 4/2002 | Luzzio et al. |
| 2002/0169165 | A1 | 11/2002 | Kath et al. |
| 2004/0158065 | A1 | 8/2004 | Barth et al. |
| 2004/0242604 | A1 | 12/2004 | Bhattacharya et al. |
| 2005/0043334 | A1* | 2/2005 | Wallace et al. ............ 514/266.2 |
| 2005/0043336 | A1 | 2/2005 | Hennequin et al. |
| 2005/0101616 | A1 | 5/2005 | Wallace et al. |
| 2005/0101617 | A1 | 5/2005 | Wallace et al. |
| 2005/0101618 | A1 | 5/2005 | Connell et al. |
| 2005/0119288 | A1 | 6/2005 | Bhattacharaya et al. |
| 2006/0025430 | A1 | 2/2006 | Mishini et al. |

FOREIGN PATENT DOCUMENTS

| | | |
|---|---|---|
| WO | WO 98/15118 | 5/1996 |
| WO | WO 96/16960 | 6/1996 |
| WO | WO 97/13771 | 4/1997 |
| WO | WO 97/30034 | 8/1997 |
| WO | WO 98/02434 | 1/1998 |
| WO | WO 99/09016 | 2/1999 |
| WO | WO 99/24440 | 5/1999 |
| WO | WO 00/31048 | 6/2000 |
| WO | WO 00-42022 | 7/2000 |
| WO | WO 01/98277 | 12/2001 |
| WO | WO 02/02552 | 1/2002 |
| WO | WO2007059257 | * 5/2007 |

OTHER PUBLICATIONS

David W. Rusnak, et al., The Effects of the Novel, Reversible Epidermal Growth Factor Receptor/ErbB-2 Tyrosine Kinase Inhibitor, GW2016, on the Growth of Human Normal and Tumor-derived Cell Lines in Vitro and in Vivo, *Molecular Cancer Therapeutics*, 2001, vol. 1 (December) pp. 85-94.

David W. Rusnak, et al., The Characterization of Novel, Dual ErbB-2/EGFR, Tyrosine Kinase Inhibitors: Potential Therapy for Cancer, *Cancer Research*, vol. 61, pp. 7196-7203, Oct. 1, 2001.

European Search Report issued in corresponding European Parent Application No. 04780990.0-2117 dated on Sep. 3, 2007.

* cited by examiner

QUINAZOLINE ANALOGS AS RECEPTOR TYROSINE KINASE INHIBITORS

BACKGROUND OF THE INVENTION

1. Field of the Invention

This invention relates to novel inhibitors of type I receptor tyrosine kinases and related kinases, pharmaceutical compositions containing the inhibitors, and methods for preparing these inhibitors. The inhibitors are useful for the treatment of hyperproliferative diseases, such as cancer and inflammation, in mammals and especially in humans.

2. Description of the State of the Art

The type I receptor tyrosine kinase family consists of four closely related receptors: EFGR (ErbB1 or HER1), ErbB2 (HER2), ErbB3 (HER), and ErbB4 (HER4) (Reviewed in Riese and Stem, *Bioessays* (1998) 20, 41-48, Olayioye et al, *EMBO* Journal (2000) 19, 3159-3167 and Schlessinger, *Cell* (2002) 110, 669-672). These are single pass transmembrane glycoprotein receptors containing an extracellular ligand binding region and an intracellular signaling domain. In addition, all receptors contain an intracellular active tyrosine kinase domain with the exception of ErbB3 whose kinase domain does not exhibit enzymatic activity. These receptors transmit extracellular signals through the cytosol to the nucleus upon activation. The activation process is initiated by ligand binding to the extacellular domain of the receptor by one of a number of different hormones. Upon ligand binding, homo- or heterodimerization is induced which results in the activation of the tyrosine kinase domains and phosphorylation of tyrosines on the intracellular signaling domains. Since no known ligand for ErbB2 has been described and ErbB3 lacks an active kinase domain, these receptors must heterodimerize to elicit a response. The phosphotyrosines then recruit the necessary cofactors to initiate several different signaling cascades including the ras/raf/MEK/MAPK and P13K/AKT pathways. The precise signal elicited will depend on what ligands are present since the intracellular signaling domains differ as to what pathways are activated. These signaling pathways lead to both cell proliferation and cell survival through inhibition of apoptosis.

Several investigators have demonstrated the role of EGFR and ErbB2 in development and cancer (Reviewed in Salomon et al, *Crit Rev Oncol Hematol* (1995) 19, 183-232, Klapper et al, *Adv. Cancer Res* (2000) 77, 25-79 and Hynes and Stern, *Biochim Biophys Acta* (1994) 1198, 165-184). Squamous carcinomas of the head and neck, and lung express high levels of EGFR. Also, constitutively active EGFR has been found in gliomas, breast cancer and lung cancer. ErbB2 overexpression occurs in approximately 30% of all breast cancer. It has also been implicated in other human cancers including colon, ovary, bladder, stomach, esophagus, lung, uterus and prostate. ErbB2 overexpression has also been correlated with poor prognosis in human cancer, including metastasis, and early relapse.

The type I tyrosine kinase receptor family have been an active area of anti-cancer research (Reviewed in Mendelsohn and Baselga, *Oncogene* (2000) 19, 6550-6565 and Normanno et al, *Endocrine-Related Cancer* (2003) 10, 1-21). Several inhibitors of the EGFR and the ErbB2 signaling pathway have demonstrated clinical efficacy in cancer treatment. Herceptin, a humanized version of anti-ErbB2 monoclonal antibody, was approved for use in breast cancer in the United States in 1998. Iressa and Tarceva are small molecule inhibitors of EGFR that are expected to be commercially available. In addition, several other antibodoes and small molecules that target the interruption of the type I tyrosine kinase receptor signaling pathways are in clinical and preclinical development. For example, IMC-225, which is a humanized antibody against the extracellular domain of EGFR demonstrated efficacy and will likely be approved.

SUMMARY OF THE INVENTION

This invention provides compounds, methods to produce these compounds, and pharmaceutical compositions containing the compounds that inhibit type I receptor tyrosine kinases. Such compounds, generally referred to as quinazoline analogs, have utility as therapeutic agents for diseases that can be treated by the inhibition of type I receptor tyrosine kinases. They may also act as inhibitors of serine, threonine, and dual specificity kinases inhibitors. In general, the invention relates to quinazoline derivatives of general Formula I:

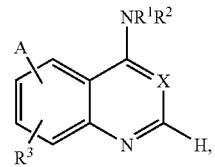

wherein an A group is bonded to at least one of the carbons at the 5, 6 7 or 8 position of the bicyclic ring, and the ring is substituted by up to three independent $R^3$ groups.

X is N, CH, CF or C—CN.

A includes Q or —$(U)_nZ$, where:

Q is

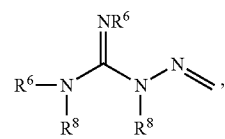

and

Z is:

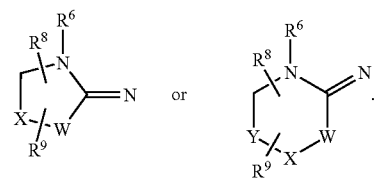

The invention may also be directed to pharmaceutically acceptable prodrugs, pharmaceutically active metabolites, and pharmaceutically acceptable salts of the compound of general Formula I. Methods of making the compounds of Formula I are also described.

In a further aspect, the present invention provides compounds that inhibit the activity of type I receptor tyrosine kinases such as EFGR, ErbB2, ErbB3, ErbB4, VEGFR2, Flt3 and FGFR, comprising compounds of Formula I.

In a further aspect, the present invention provides a method of treating diseases or medical conditions mediated by type I receptor tyrosine kinases which comprises administering to a warm-blooded animal an effective amount of a compound of Formula I, or a pharmaceutically acceptable salt or in vivo cleavable prodrug thereof.

In a further aspect, the present invention provides a method of inhibiting the production of type I receptor kinases which comprises administering to a warm-blooded animal an effective amount of a compound of Formula I, or a pharmaceutically acceptable salt or in vivo cleavable prodrug thereof.

In a further aspect, the present invention provides a method of providing type I receptor kinase inhibitory effect comprising administering to a warm-blooded animal an effective amount of a compound of Formula I, or a pharmaceutically acceptable salt or in vivo cleavable prodrug thereof.

In a further aspect, the present invention provides treating or preventing a type I receptor kinase mediated condition, comprising administering an amount of a compound effective to treat or prevent said type I receptor kinase-mediated condition or a pharmaceutical composition comprising said compound, to a human or animal in need thereof, wherein said compound is a compound of Formula I, or a pharmaceutically-acceptable salt or in vivo cleavable prodrug thereof. The type I receptor kinase mediated condition that can be treated according to the methods of this invention includes hyperproliferative disorders, such as cancer of the head and neck, lung, breast, colon, ovary, bladder, stomach, esophagus, uterus or prostate, among other kinds of hyperproliferative disorders.

The compounds of Formula I may be used advantageously in combination with other known therapeutic agents.

The invention also relates to pharmaceutical compositions comprising an effective amount of an agent selected from compounds of Formula I or a pharmaceutically acceptable prodrug, pharmaceutically active metabolite, or pharmaceutically acceptable salt thereof.

Additional advantages and novel features of this invention shall be set forth in part in the description that follows, and in part will become apparent to those skilled in the art upon examination of the following specification, or may be learned by the practice of the invention. The advantages of the invention may be realized and attained by means of the instrumentalities, combinations, compositions, and methods particularly pointed out in the appended claims.

BRIEF DESCRIPTION OF THE FIGURES

The accompanying drawings, which are incorporated herein and form a part of the specification, illustrate non-limiting embodiments of the present invention, and together with the description, serve to explain the principles of the invention.

In the Figures.

DETAILED DESCRIPTION OF THE INVENTION

Figure 1:
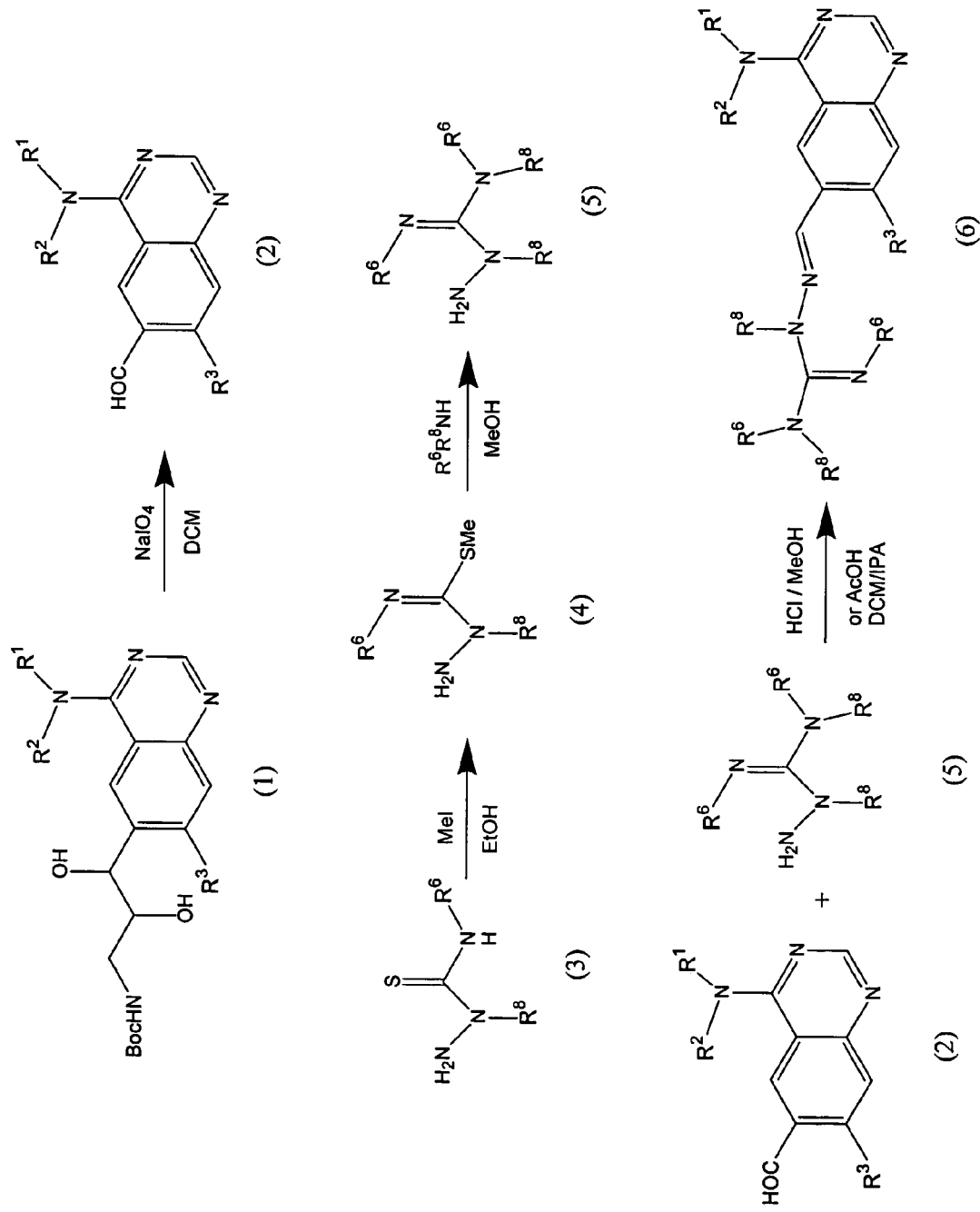
FIG. 1 shows a reaction scheme for the preparation of imino guanidines.

The inventive compounds of Formula I are useful for inhibiting type I receptor tyrosine kinases, such as EFGR (HER1), ErbB2 (HER2), ErbB3 (HER3), ErbB4 (HER4), VEGFR2, Flt3 and FGFR. The compounds of Formula I may also be useful as inhibitors of serine, threonine, and dual specificity kinases such as Raf, MEK, and p38. Such compounds have utility as therapeutic agents for diseases that can be treated by the inhibition of the type I receptor tyrosine kinases signaling pathway and serine, threonine, and dual specificity kinase pathways. In general, the invention relates to compounds of the general Formula I:

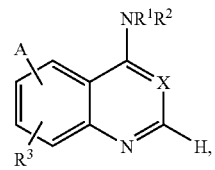

wherein an A group is bonded to at least one of the carbons at the 5, 6, 7 or 8 position, preferably the 6 or 7 position, of the bicyclic ring, and the ring is substituted by up to three independent $R^3$ groups;

X is N, CH, CF or C—CN.

$R^1$ is a substituted or unsubstituted, monocyclic or bicyclic, aryl or heteroaryl moiety and $R^2$ is H or a substituted or unsubstituted $C_{1-8}$ alkyl. $R^2$ may also be a $C_{1-8}$ alkyl having a terminal carbon atom bound to one of the ring atoms of $R^1$.

$R^3$ is is hydrogen, halogen, cyano, nitro, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl, heterocyclylalkyl, —$NR^4SO_2R^5$, —$SO_2NR^6R^4$, —$C(O)R^6$, —$C(O)OR^6$, —$OC(O)R^6$, —$NR^4C(O)OR^5$, —$NR^4C(O)R^6$, —$C(O)NR^4R^6$, —$NR^4R^6$, —$NR^4C(O)NR^4R^6$, —$OR^6$, —$S(O)R^5$, —$SO_2R^5$, where each of the above alkyl, alkenyl, alkynyl, cycloalkyl, aryl, heteroaryl and heterocyclyl portion of $R^3$ is optionally substituted with one to five groups independently selected from oxo, halogen, cyano, nitro, trifluoromethyl, difluoromethoxy, trifluoromethoxy, azido, —$NR^4SO_2R^5$, —$SO_2NR^6R^4$, —$C(O)R^6$, —$C(O)OR^6$, —$OC(O)R^6$, —$NR^4C(O)OR^5$, —$NR^4C(O)CR^6$, —$C(O)NR^4R^6$, —$NR^4R^6$, —$NR^4C(O)NR^4R^6$, —$NR^4C(NCN)NR^4R^6$, —$OR^6$, —$S(O)R^5$, —$SO_2R^5$, aryl, arylalkyl, heteroaryl, heteroarylalkyl, heterocyclyl, and heterocyclylalkyl.

A is Q or —$(U)_nZ$, where

Q is

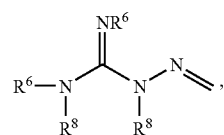

and n is 0 or 1, and U is $C_1$-$C_4$ alkyl, $C_2$-$C_4$ alkenyl or $C_2$-$C_4$ alkynyl; where each alkyl, alkenyl or alkynyl is optionally substituted with up to five groups independently selected from oxo, halogen, cyano, nitro, trifluoromethyl, difluoromethoxy, trifluoromethoxy, azido, —$NR^4SO_2R^5$, —$SO_2NR^6R^4$, —$C(O)R^6$, —$C(O)OR^6$, —$OC(O)R^6$, —$NR^4C(O)OR^5$, —$NR^4C(O)CR^6$, —$C(O)NR^4R^6$, —$NR^4R^6$, —$NR^4C(O)NR^4R^6$, —$NR^4C(NCN)NR^4R^6$, —$OR^6$, —$S(O)R^5$, —$SO_2R^5$, aryl, arylalkyl, heteroaryl, heteroarylalkyl, heterocyclyl, and heterocyclylalkyl.

Z is

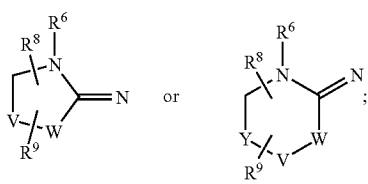

where W, V and Y are selected independently from $CR^7R^8$, $CR^8R^9$, O, $NR^6$, S, SO, $SO_2$, provided: If W is O, $NR^6$, S, SO, $SO_2$, then V is $CR^8R^9$, if X is O, $NR^6$, S, SO, $SO_2$, then W and Y are each $CR^8R^9$, and if Y is O, $NR^6$, S, SO, $SO_2$, then V is $CR^8R^9$.

Z includes one or more $R^8$ or $R^9$ groups, wherein said $R^8$ and $R^9$ groups may be bonded to the same or different atoms.

$R^4$ is H or $C_{1-6}$ alkyl.

$R^5$ is trifluoromethyl, $C_1$-$C_{10}$ alkyl, $C_3$-$C_{10}$ cycloalkyl, aryl, arylalkyl, heteroaryl, heteroarylalkyl, heterocyclyl, heterocyclylalkyl, where each alkyl, cycloalkyl, aryl, heteroaryl, heterocyclyl and heterocyclylalkyl is optionally substituted with one to five groups independently selected from oxo, halogen, cyano, nitro, $OR^6$, $NR^4R^6$, trifluoromethyl, difluoromethoxy, trifluoromethoxy, azido, aryl, heteroaryl, arylalkyl, heteroarylalkyl, heterocyclyl, and heterocyclylalkyl.

$R^6$, $R^8$ and $R^9$ are each, hydrogen, trifluoromethyl, $C_1$-$C_{10}$ alkyl, $(CH_2)_{0-4}C_3$-$C_{10}$ cycloalkyl, aryl, arylalkyl, heteroaryl, heteroarylalkyl, heterocyclyl, heterocyclylalkyl, where each alkyl, cycloalkyl, aryl, heteroaryl and heterocyclyl is optionally substituted with one to five groups independently selected from oxo, halogen, cyano, nitro, $OR^6$, $NR^6R^6$, trifluoromethyl, difluoromethoxy, trifluoromethoxy, azido, aryl, heteroaryl, arylalkyl, heteroarylalkyl, heterocyclyl, and heterocyclylalkyl.

$R^7$ is the same as $R^3$.

The compound of Formula I may also include an $R^4$ group and an $R^6$ group, that are independently joined to complete a 3 to 10 membered cyclic ring optionally containing additional heteroatoms selected from the group consisting of O, S, SO, $SO_2$ and $NR^6$ where each ring carbon may be optionally substituted with one to three groups independently selected from halogen, cyano, nitro, trifluoromethyl, difluoromethoxy, trifluoromethoxy, azido, aryl, $OR^8$, $NR^6R^8$, heteroaryl, arylalkyl, heteroarylalkyl, heterocyclyl, and heterocyclylalkyl; provided said ring does not contain two adjacent O or two adjacent S atoms.

The compound of Formula I may also include an $R^6$ group and an $R^8$ group, that are independently joined to complete a 3 to 10 membered cyclic ring optionally containing additional heteroatoms selected from the group consisting of O, S, SO, $SO_2$ and $NR^6$ where each ring carbon may be optionally substituted with one to three groups independently selected from halogen, cyano, nitro, trifluoromethyl, difluoromethoxy, trifluoromethoxy, azido, aryl, $OR^8$, $NR^6R^8$, heteroaryl, arylalkyl, heteroarylalkyl, heterocyclyl, and heterocyclylalkyl; provided said ring does not contain two adjacent O or two adjacent S atoms.

The compound of Formula I may also include an $R^7$ group and an $R^8$ group, that are independently joined to complete a 3 to 10 membered cyclic ring optionally containing additional heteroatoms selected from the group consisting of O, S, SO, $SO_2$ and $NR^6$ where each ring carbon may be optionally substituted with one to three groups independently selected from halogen, cyano, nitro, trifluoromethyl, difluoromethoxy, trifluoromethoxy, azido, aryl, $OR^8$, $NR^6R^8$, heteroaryl, arylalkyl, heteroarylalkyl, heterocyclyl, and heterocyclylalkyl; provided said ring does not contain two adjacent O or two adjacent S atoms.

The compound of Formula I may also include an $R^8$ group and an $R^9$ group, that are independently joined to complete a 3 to 10 membered cyclic ring optionally containing additional heteroatoms selected from the group consisting of O, S, SO, $SO_2$ and $NR^6$ where each ring carbon may be optionally substituted with one to three groups independently selected from halogen, cyano, nitro, trifluoromethyl, difluoromethoxy, trifluoromethoxy, azido, aryl, $OR^8$, $NR^6R^8$, heteroaryl, arylalkyl, heteroarylalkyl, heterocyclyl, and heterocyclylalkyl; provided said ring does not contain two adjacent O or two adjacent S atoms.

The term "alkyl" as used herein refers to a saturated linear or branched-chain monovalent hydrocarbon radical of one to twelve carbon atoms, wherein the alkyl radical may be optionally substituted independently with one or more substituents described below. Examples of alkyl groups include, but are not limited to, methyl, ethyl, n-propyl, isopropyl, butyl, isobutyl, sec-butyl, tert-butyl, pentyl, isopentyl, tert-pentyl, hexyl, isohexyl, and the like.

"Alkylene" means a linear or branched saturated divalent hydrocarbon radical of one to twelve carbon atoms, e.g., methylene, ethylene, propylene, 2-methylpropylene, pentylene, and the like.

The term "alkenyl" refers to linear or branched-chain monovalent hydrocarbon radical of two to twelve carbon atoms, containing at least one double bond, e.g., ethenyl, propenyl, and the like, wherein the alkenyl radical may be optionally substituted independently with one or more substituents described herein, and includes radicals having "cis" and "trans" orientations, or alternatively, "E" and "Z" orientations.

The term "alkenylene" refers to a linear or branched divalent hydrocarbon radical of two to twelve carbons containing at least one double bond, wherein the alkenylene radical may be optionally substituted independently with one or more substituents described herein. Examples include, but are not limited to, ethenylene, propenylene, and the like.

The term "alkynyl" refers to a linear or branched monovalent hydrocarbon radical of two to twelve carbon atoms containing at least one triple bond. Examples include, but are not limited to, ethynyl, propynyl, and the like, wherein the alkynyl radical may be optionally substituted independently with one or more substituents described herein.

The term "alkynylene" to a linear or branched divalent hydrocarbon radical of two to twelve carbons containing at least one triple bond, wherein the alkynylene radical may be optionally substituted independently with one or more substituents described herein.

The term "allyl" refers to a radical having the formula RC=CHCHR, wherein R is alkyl, alkenyl, alkynyl, cycloalkyl, heterocycloalkyl, aryl, heteroaryl, or any substituent as defined herein, wherein the allyl may be optionally substituted independently with one or more substituents described herein.

The term "cycloalkyl" refers to saturated or partially unsaturated cyclic hydrocarbon radical having from three to twelve carbon atoms, wherein the cycloalkyl may be optionally substituted independently with one or more substituents described herein. The term "cycloalkyl" further includes bicyclic and tricyclic cycloalkyl structures, wherein the bicyclic and tricyclic structures may include a saturated or partially unsaturated cycloalkyl fused to a saturated or partially unsaturated cycloalkyl or heterocycloalkyl ring or an aryl or heteroaryl ring. Examples of cycloalkyl groups include, but are not limited to, cyclopropyl, cyclobutyl, cyclopentyl, cyclohexyl, cycloheptyl, and the like.

The term "heteroalkyl" refers to saturated linear or branched-chain monovalent hydrocarbon radical of one to twelve carbon atoms, wherein at least one of the carbon atoms is replaced with a heteroatom selected from N, O, or S, and wherein the radical may be a carbon radical or heteroatom radical (i.e., the heteroatom may appear in the middle or at the end of the radical). The heteroalkyl radical may be optionally substituted independently with one or more substituents described herein. The term "heteroalkyl" encompasses alkoxy and heteroalkoxy radicals.

The term "heterocycloalkyl" refers to a saturated or partially unsaturated cyclic radical of 3 to 8 ring atoms in which at least one ring atom is a heteroatom selected from nitrogen, oxygen and sulfur, the remaining ring atoms being C where one or more ring atoms may be optionally substituted independently with one or more substituent described below. The radical may be a carbon radical or heteroatom radical. "Heterocycloalkyl" also includes radicals where heterocycle radicals are fused with aromatic or heteroaromatic rings. Examples of heterocycloalkyl rings include, but are not limited to, pyrrolidine, piperidine, piperazine, tetrahydropyranyl, morpholine, thiomorpholine, homopiperazine, phthalimide, and derivatives thereof.

The term "heteroalkenyl" refers to linear or branched-chain monovalent hydrocarbon radical of two to twelve carbon atoms, containing at least one double bond, e.g., ethenyl, propenyl, and the like, wherein at least one of the carbon atoms is replaced with a heteroatom selected from N, O, or S, and wherein the radical may be a carbon radical or heteroatom radical (i.e., the heteroatom may appear in the middle or at the end of the radical). The heteroalkenyl radical may be optionally substituted independently with one or more substituents described herein, and includes radicals having "cis" and "trans" orientations, or alternatively, "E" and "Z" orientations.

The term "heteroalkynyl" refers to a linear or branched monovalent hydrocarbon radical of two to twelve carbon atoms containing at least one triple bond. Examples include, but are not limited to, ethynyl, propynyl, and the like, wherein at least one of the carbon atoms is replaced with a heteroatom selected from N, O, or S, and wherein the radical may be a carbon radical or heteroatom radical (i.e., the heteroatom may appear in the middle or at the end of the radical). The heteroalkynyl radical may be optionally substituted independently with one or more substituents described herein.

The term "heteroallyl" refers to radicals having the formula RC=CHCHR, wherein R is alkyl, alkenyl, alkynyl, cycloalkyl, heterocycloalkyl, aryl, heteroaryl, or any substituent as defined herein, wherein at least one of the carbon atoms is replaced with a heteroatom selected from N, O, or S, and wherein the radical may be a carbon radical or heteroatom radical (i.e., the heteroatom may appear in the middle or at the end of the radical). The heteroallyl may be optionally substituted independently with one or more substituents described herein.

"Aryl" means a monovalent aromatic hydrocarbon monocyclic radical of 6 to 10 ring atoms or a polycyclic aromatic hydrocarbon, optionally substituted independently with one or more substituents described herein. More specifically the term aryl includes, but is not limited to, phenyl, 1-naphthyl, 2-naphthyl, and derivatives thereof.

"Heteroaryl" means a monovalent monocyclic aromatic radical of 5 to 10 ring atoms or a polycyclic aromatic radical, containing one or more ring heteroatoms selected from N, O, or S, the remaining ring atoms being C. The aromatic radical is optionally substituted independently with one or more substituents described herein. Examples include, but are not limited to, furyl, thienyl, pyrrolyl, pyridyl, pyrazolyl, pyrimidinyl, imidazolyl, pyrazinyl, indolyl, thiophen-2-yl, quinolyl, benzopyranyl, thiazolyl, and derivatives thereof.

The term "halo" represents fluoro, chloro, bromo or iodo. Likewise, the term "halogen" refers to a fluorine, chlorine, bromine, or iodine substituent.

In general, the various moieties or functional groups of the compounds of Formula I may be optionally substituted by one or more substituents. Examples of substituents suitable for purposes of this invention include, but are not limited to, halo, alkyl, allyl, alkenyl, alkynyl, heteroalkyl, heteroallyl, heteroalkenyl, heteroalkynyl, alkoxy, heteroalkoxy, $G_n$-cycloalkyl, $G_n$ heterocycloalkyl, $G_n$-OR, $G_n$-NO2, $G_n$-CN, $G_n$-CO$_2$R, $G_n$-(C=O)R, $G_n$-O(C=O)R, $G_n$-O-alkyl, $G_n$-OAr, $G_n$-SH, $G_n$-SR, $G_n$-SOR, $G_n$-SO$^2$R, $G_n$-S—Ar $G_n$-SOAr, $G_n$-SO$_2$Ar, aryl, heteroaryl, $G_n$-Ar, $G_n$-(C=O) NR$^2$R$^3$, $G_n$-NR$^2$R$^3$, $G_n$-NR(C=O)R, $G_n$-SO$_2$NR$^2$R$^3$, PO$_3$H$_2$, SO$_3$H$_2$, where: G is alkylene having from 1 to 4 carbons, or alkenylene or alkynylene each having from 2 to 4 carbons, wherein said alkylene, alkenylene, or alkynylene may be substituted or unsubstituted; n is zero or 1, R$^1$, R$^2$, and R$^3$ are alkyl, allyl, alkenyl, alkynyl, heteroalkyl, heteroallyl, heteroalkenyl, heteroalkynyl, alkoxy, heteroalkoxy, $G_n$-cycloalkyl, or $G_n$-heterocycloalkyl, and Ar is aryl or heteroaryl, wherein said alkyl, allyl, alkenyl, alkynyl, heteroalkyl, heteroallyl, heteroalkenyl, heteroalkynyl, alkoxy, heteroalkoxy, $G_n$-cycloalkyl, $G_n$-heterocycloalkyl, Ar, R$^1$, R$^2$, and R$^3$ may be further substituted or unsubstituted.

The compounds of this invention may possess one or more asymmetric centers; such compounds can therefore be produced as individual (R)— or (S)-stereoisomers or as mixtures thereof. Unless indicated otherwise, the description or naming of a particular compound in the specification and claims is intended to include both individual enantiomers and mixtures, racemic or otherwise, thereof. Accordingly, this invention also includes racemates and resolved enantiomers, and diastereomers compounds of the Formula I. The methods for the determination of stereochemistry and the separation of stereoisomers are well known in the art (see discussion in Chapter 4 of "Advanced Organic Chemistry", 4 th edition J. March, John Wiley and Sons, New York, 1992).

In addition to compounds of the Formula I, the invention also includes solvates, pharmaceutically acceptable prodrugs, pharmaceutically active metabolites, and pharmaceutically acceptable salts of such compounds.

The term "solvate" refers to an aggregate of a molecule with one or more solvent molecules.

A "pharmaceutically acceptable prodrug" is a compound that may be converted under physiological conditions or by solvolysis to the specified compound or to a pharmaceutically acceptable salt of such compound.

A "pharmaceutically active metabolite" is a pharmacologically active product produced through metabolism in the body of a specified compound or salt thereof. Metabolites of a compound may be identified using routine techniques known in the art and their activities determined using tests such as those described herein.

Prodrugs and active metabolites of a compound may be identified using routine techniques known in the art. Various forms of prodrugs are known in the art. For examples of such prodrug derivatives, see, for example, a) *Design of Prodrugs*, edited by H. Bundgaard, (Elsevier, 1985) and *Methods in Enzymology*, Vol. 42, p. 309-396, edited by K. Widder, et al. (Academic Press, 1985); b) *A Textbook of Drug Design and*

*Development*, edited by Krogsgaard-Larsen and H. Bundgaard, Chapter 5 *"Design and Application of Prodrugs"*, by H. Bundgaard p. 113-191 (1991); c) H. Bundgaard, *Advanced Drug Delivery Reviews*, 8, 1-38 (1992); d) H. Bundgaard, et al., *Journal of Pharmaceutical Sciences*, 77:285 (1988); and e) N. Kakeya, et al., *Chem. Pharm. Bull.*, 32: 692 (1984), each of which is specifically incorporated herein by reference.

A "pharmaceutically acceptable salt" is a salt that retains the biological effectiveness of the free acids and bases of the specified compound and that is not biologically or otherwise undesirable. A compound of the invention may possess a sufficiently acidic, a sufficiently basic, or both functional groups, and accordingly react with any of a number of inorganic or organic bases, and inorganic and organic acids, to form a pharmaceutically acceptable sale. Examples of pharmaceutically acceptable salts include those salts prepared by reaction of the compounds of the present invention with a mineral or organic acid or an inorganic base, such salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyn-1,4-dioates, hexyne-1,6-dioates, benzoates, chlorobenzoates, methylbenzoates, dinitromenzoates, hydroxybenzoates, methoxybenzoates, phthalates, sulfonates, xylenesulfonates, pheylacetates, phenylpropionates, phenylbutyrates, citrates, lactates, γ-hydroxybutyrates, glycollates, tartrates, methanesulfonates, propanesulfonates, naphthalene-1-sulfonates, naphthalene-2-sulfonates, and mandelates.

If the inventive compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid such as glucuronic acid or galacturonic acid, an alphahydroxy acid such as citric acid or tartaric acid, an amino acid such as aspartic acid or glutamic acid, an aromatic acid such as benzoic acid or cinnamic acid, a sulfonic acid such as p-toluenesulfonic acid or ethanesulfonic acid, or the like.

If the inventive compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The inventive compounds may be prepared using the reaction routes and synthesis schemes as described below, employing the techniques available in the art using starting materials that are readily available.

Therapeutic Aspects of the Invention

Therapeutically effective amounts of the compounds of the invention may be used to treat diseases mediated by modulation or regulation of type I receptor tyrosine kinases and/or serine, threonine, and/or dual specificity kinases. : An "effective amount" is intended to mean that amount of compound that, when administered to a mammal in need of such treatment, is sufficient to effect treatment for a disease mediated by the activity of one or more type I receptor tyrosine kinases and/or serine, threonine, and/or dual specificity kinases. Thus, for example, a therapeutically effective amount of a compound selected from Formula I or a salt, active metabolite or prodrug thereof, is a quantity sufficient to modulate, regulate, or inhibit the activity of one or more type I receptor tyrosine kinases and/or serine, threonine, and/or dual specificity kinases such that a disease condition which is mediated by that activity is reduced or alleviated.

The amount of a given agent that will correspond to such an amount will vary depending upon factors such as the particular compound, disease condition and its severity, the identity (e.g., weight) of the mammal in need of treatment, but can nevertheless be routinely determined by one skilled in the art. "Treating" is intended to mean at least the mitigation of a disease condition in a mammal, such as a human, that is affected, at least in part, by the activity of one or more type I receptor tyrosine kinases and/or serine, threonine, and/or dual specificity kinases, and includes, but is not limited to, preventing the disease condition from occurring in a mammal, particularly when the mammal is found to be predisposed to having the disease condition but has not yet been diagnosed as having it; modulating and/or inhibiting the disease condition; and/or alleviating the disease condition.

In order to use a compound of the Formula I, or a pharmaceutically acceptable salt or in vivo cleavable prodrug thereof, for the therapeutic treatment (including prophylactic treatment) of mammals including humans, it is normally formulated in accordance with standard pharmaceutical practice as a pharmaceutical composition. According to this aspect of the invention there is provided a pharmaceutical composition that comprises a compound of the Formula I, or a pharmaceutically acceptable salt or in vivo cleavable prodrug thereof, as defined hereinbefore in association with a pharmaceutically acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, or intramuscular dosing or as a suppository for rectal dosing). For example, compositions intended for oral use may contain one or more coloring, sweetening, flavoring and/or preservative agents.

Suitable pharmaceutically-acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), coloring agents, flavoring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent, and one or more preservatives. Suitable dispersing or wetting agents and suspending agents are exemplified by those already mentioned above. Additional excipients such as sweetening, flavoring and coloring agents, may also be present.

The pharmaceutical compositions of the invention may also be in the form of oil-in-water emulsions. The oily phase may be a vegetable oil, such as olive oil or arachis oil, or a mineral oil such as liquid paraffin, or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavoring and preservative agents.

Syrups and elixirs may be formulated with sweetening agents such as glycerol, propylene glycol, sorbitol, aspartame or sucrose, and may also contain a demulcent, preservative, flavoring and/or coloring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipient, which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedures well known in the art.

Compositions for administration by insufflation may be in the form of a finely divided powder containing particles of average diameter of, for example, 30 µm or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurized aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulations, see Chapter 25.2 in Volume 5 of Comprehensive Medicinal Chemistry (Corwin Hansch; Chairman of Editorial Board), Pergamon Press 1990, which is specifically incorporated herein by reference.

The amount of a compound of this invention that is combined with one or more excipients to produce a single dosage form will necessarily vary depending upon the host treated and the particular route of administration. For example, a formulation intended for oral administration to humans may contain, for example, from 0.5 mg to 2 g of active agent compounded with an appropriate and convenient amount of excipients, which may vary from about 5 to about 98 percent by weight of the total composition. Dosage unit forms will generally contain about 1 mg to about 500 mg of an active ingredient. For further information on routes of administration and dosage regimes, see Chapter 25.3 in Volume 5 of *Comprehensive Medicinal Chemistry* (Corwin Hansch; Chairman of Editorial Board), Pergamon Press 1990, which is specifically incorporated herein by reference.

The size of the dose for therapeutic or prophylactic purposes of a compound of Formula I will naturally vary according to the nature and severity of the conditions, the age and sex of the animal or patient and the route of administration, according to well known principles of medicine.

Although the compounds of Formula I are primarily of value as therapeutic agents for use in warm-blooded animals (including man), they are also useful whenever it is required to control type I receptor tyrosine kinases and/or serine, threonine, and/or dual specificity kinases. Thus, they are useful as pharmacological standards for use in the development of new biological tests and in the search for new pharmacological agents.

The activity of the compounds of this invention may be assayed for type I receptor tyrosine kinases inhibition and/or serine, threonine, and/or dual specificity kinases in vitro, in vivo, or in a cell line. In vitro assays include assays that determine inhibition of the kinase activity. Alternate in vitro assays quantitate the ability of the inhibitor to bind to kinases and may be measured either by radiolabelling the inhibitor prior to binding, isolating the inhibitor/kinase complex and determining the amount of radiolabel bound, or by running a competition experiment where new inhibitors are incubated with known radioligands. These and other useful in vitro and cell culture assays are well known to those of skill in the art.

Although the invention has been described and illustrated with a certain degree of particularity, it is understood that the present disclosure has been made only by way of example, and that numerous changes in the combination and arrangement of parts can be resorted to by those skilled in the art without departing from the spirit and scope of the invention, as hereinafter claimed.

BIOLOGICAL EXAMPLES

EGFR/ErbB2 Enzymatic Assays

Thermo LabSystems Immulon 4HBX 96-well plates are coated by incubation overnight at room temperature with 100 µL per well of 0.25 mg/mL Poly (Glu, Tyr) 4:1 (PGT) (Sigma Chemical Co., St. Louis, Mo.) in PBS (phosphate buffered saline). Excess PGT is removed by aspiration, and the plate is washed three times with wash buffer (0.1% Tween 20 in PBS). The kinase reaction is performed in 100 µL of 50 mM HEPES (pH 7.3) containing 125 mM sodium chloride, 24 mM magnesium chloride, 0.1 mM sodium orthovanadate, 15 µM ATP (adenosine triphosphate) and 0.3 units/mL EGFR (epidermal growth factor receptor) (BIOMOL Research Laboratories, Inc., Plymouth Meeting, Pa.). The compound in DMSO (dimethylsulfoxide) is added to give a final DMSO concentration of about 1%. Phosporylation is initiated by the addition of ATP and incubated for 30 minutes at room temperature. The kinase reaction is terminated by aspiration of the reaction mixture and subsequent washing with wash buffer (see above). Phosphorylated PGT is detected by 30 incubation with 100 µL per well HRP conjugated PY20 antiphosphotyrosine antibody (Zymed Laboratories, Inc., South San Francisco, Calif.) diluted to 0.2 µg/mL in 3% BSA and 0.05% Tween 20 in PBS. Antibody is removed by aspiration, and the plate is washed with wash buffer. The calorimetric signal is developed by the addition of 100 µL per well TMB Microwell Peroxidase Substrate (Kirkegaard and Perry, Gaithersburg, Md.), and stopped by the addition of 100 µL per well 1M phosphoric acid. Phosphotyrosine in measured by absorbance at 450 nm.

The erbB2 kinase is as above using 250 ng/mL erbB2 intracellular domain in place of EGFR. The intracellular domain of the erbB2 tyrosine kinase (amino acids 691-1255) is expressed as a his-tagged protein in Baculovirus and purified by nickel chelating, ion exchange and size exclusion chromatography.

Compounds of the present invention have $IC_{50}$'s from less than 1 nM to 50 mM.

PREPARATIVE EXAMPLES

An illustration of the preparation of compounds of the present invention is shown in FIGS. 1-5.

FIG. 1 illustrates the synthesis of imino guanidine compounds of the present invention. Aldehyde (2) can be prepared by oxidative cleavage with reagents known to those of skill in the art such as $Pb(OAc)_4$, $MnO_2$ or PCC. The aldehyde can be prepared most preferably by reaction with aqueous slurries of $NaIO_4$ in organic solvents like methylene chloride. Hydrazinecarboxoimidothioic methyl esters (4) can be prepared by reaction with alkylating agents such as methyl p-toluenesulfonate or dimethyl sulfate, most preferably with MeI, in alcoholic solvents such as EtOH or MeOH. Hydrazinecarboxoimidates (5) are prepared by addition of amines in alcoholic solvents like MeOH or EtOH at room temperature or under mild heating (e.g., 50 to 70° C.). Couplings to form imino guanidines (6) can be accomplished by heating in alcoholic solvents like MeOH or EtOH or in the presence of aqueous acid like HBr or AcOH in alcoholic solvents at room or elevated temperatures. Most preferably, compounds 6 can be prepared by coupling compounds (2) and (5) in the presence of solutions of either concentrated HCl in MeOH or glacial acetic acid in methylene chloride/iPrOH mixtures at room temperature.

Figure 2:
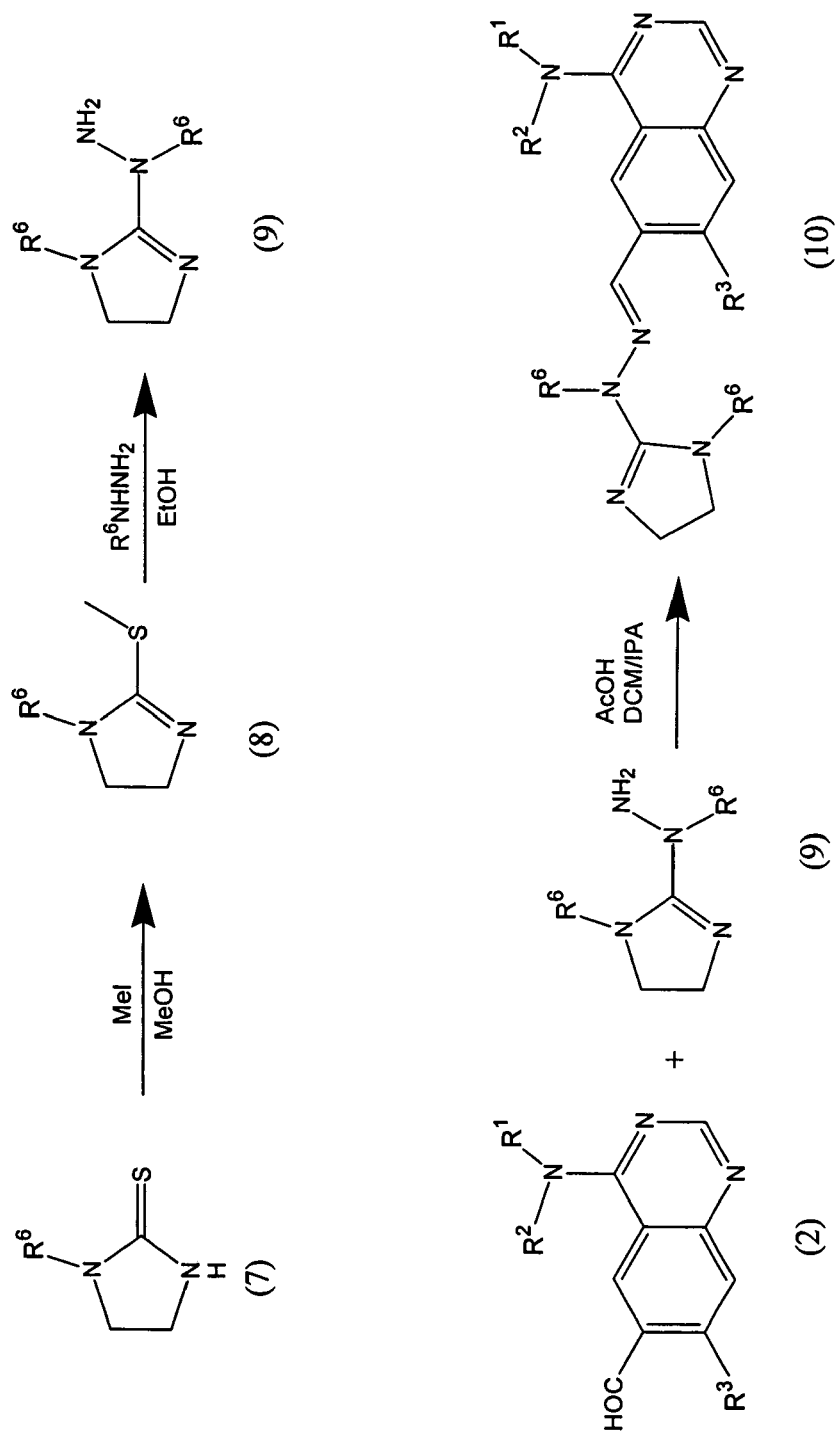
FIG. 2 shows another reaction scheme for the preparation of imino guanidines.

FIG. 2 illustrates another synthesis of imino guanidine compounds of the present invention. In the first step, methylsulfanyl-imidazoles (8) can be prepared from imidazoline-2-thiones (7) by alkylation in either neutral or basic conditions with dimethyl sulfate or MeI in alcoholic solvents such as MeOH or EtOH at room or elevated temperatures. Most preferably, compounds (8) can be prepared from imidazoline-2-thiones (7) by alkylation with MeI in MeOH at 60° C. IN the next step, imididazolyl-hydrazines (9) are prepared by addition of amines in alcoholic solvents like MeOH or EtOH at room temperature or under mild heating (50 to 70° C.). Couplings to form imino guanidines (10) can be accomplished by heating in alcoholic solvents like MeOH or EtOH or in the presence of aqueous acid like HBr or AcOH in alcoholic solvents at room or elevated temperatures. Most preferably, compounds (10) can be prepared by coupling compounds (2) and (9) in the presence of glacial acetic acid in methylene chloride/iPrOH mixtures at room temperature.

Figure 3:
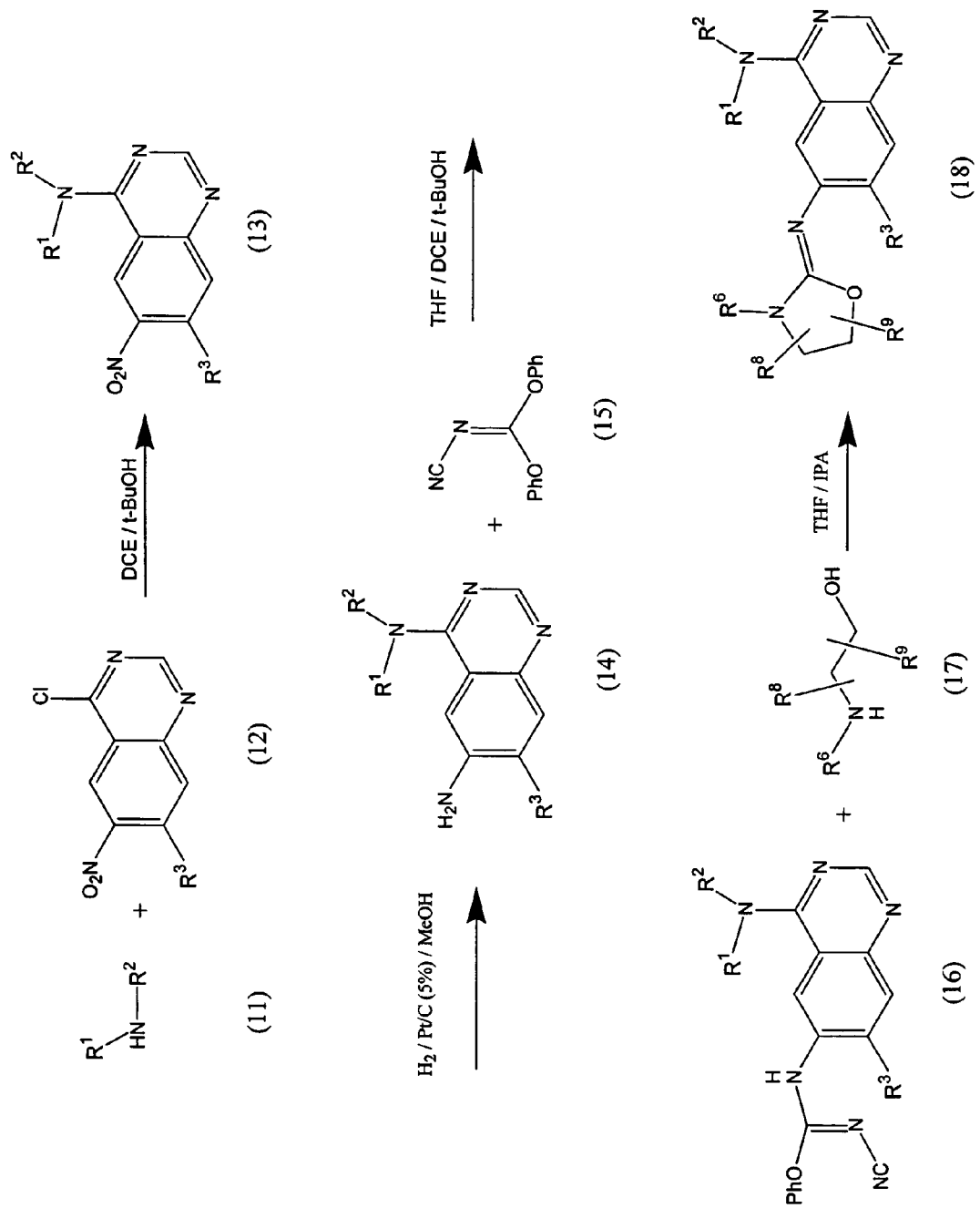
FIG. 3 shows a reaction scheme for the preparation of isoureas.

Isourea compounds of formula I can be prepared as outlined in FIG. 3. Nitro quinazolines (13) can be prepared by coupling amines (11) with chloro quinazolines (12) at either room or elevated temperature with and without additional amine bases like $Et_3N$ in organic solvents like benzene, xylene, iPrOH, or EtOH. Preferably, quinazolines (13) can be prepared from compounds (11) and (12) in a solvent mixture of DCE/tBuOH at 80-90° C. The nitro group of compound (13) can be reduced by standard procedures including but not limited to Zn dust in AcOH or aqueous $NH_4Cl/MeOH$, $SnCl_2$, Pd/C and $H_2$, $Pd(OH)_2/C$ and $H_2$ in appropriate organic solvents to give the aniline (14). As would be apparent to one of skill in the art, the choice of method of reduction will be influenced by the nature of the substituents $R^1$, $R^2$, $R^3$ present. Preferably, the reduction is accomplished by Pt/C (5% wet) and $H_2$ (1 atm) in MeOH and aqueous NaOH. The cyanoisourea (16) can be prepared by coupling aniline (14) and diphenyl N-cyanocarbonimidate (15) with or without a base such as NaH or $Et_3N$ in organic solvents such as DMF, MeCN, dioxane, pyridine, iPrOH or methylene chloride at room or elevated temperatures. Most preferably, cyanoisourea 16 is formed by coupling compounds (14) and (15) in a mixture of THF/DCE/tBuOH at 80-90° C. Isourea (18) can be prepared by coupling amino alcohol (17) and cyanoisourea (16) in a variety of organic solvents including THF and iPrOH. Preferably, the coupling of (16) and (17) is accomplished in a mixture of THF:iPrOH at elevated temperature.

Figure 4:
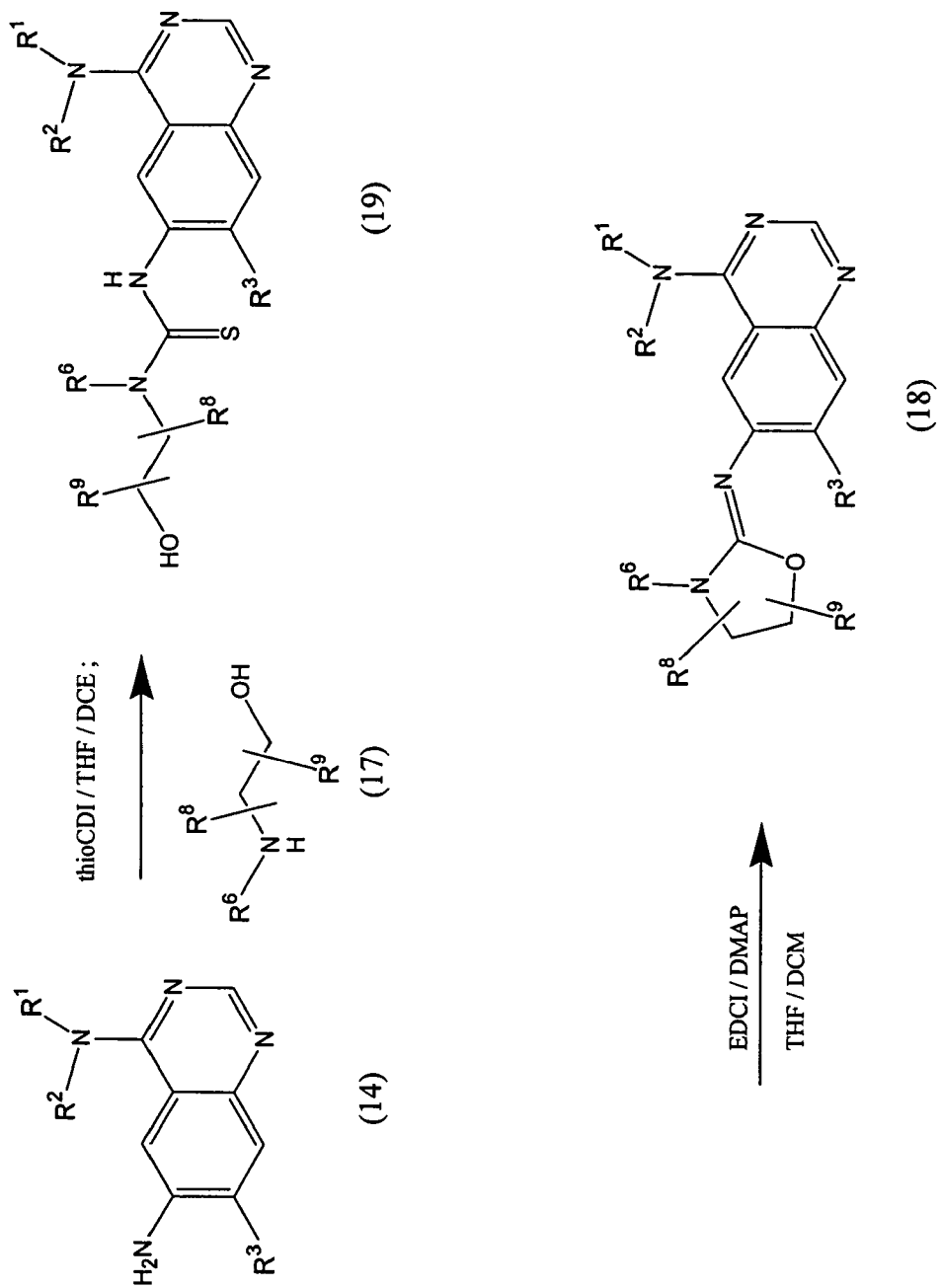
FIG. 4 shows another reaction scheme for the preparation of isoureas.

Alternatively, isourea compounds of formula I can also be prepared as outlined in FIG. 4. Thiourea (19) can be prepared by treating aniline (14) with 1,1-thiocarbonyldiimidzole in organic solvents such as THF, DCE, and DCM following by addition of amino alcohol (17). Most preferably, thiourea (19) is prepared by addition of 1,1 -thiocarbonyldiimidzole in a solution of a mixture of THF and DCE, followed by the addition of amino alcohol (17) accomplished at room temperature. Cyclization of thiourea (17) to form isourea (18) can be achieved by treatment with standard activating agents such as but not limited to MeI, DCC, and EDCI at room or elevated temperature in organic solvents such as DMF, THF, DCM, and DCE. Preferably, cyclization to form isourea (18) is accomplished by addition of EDCI with DMAP in a mixture of THF and DCE at 70-80° C.

Figure 5:
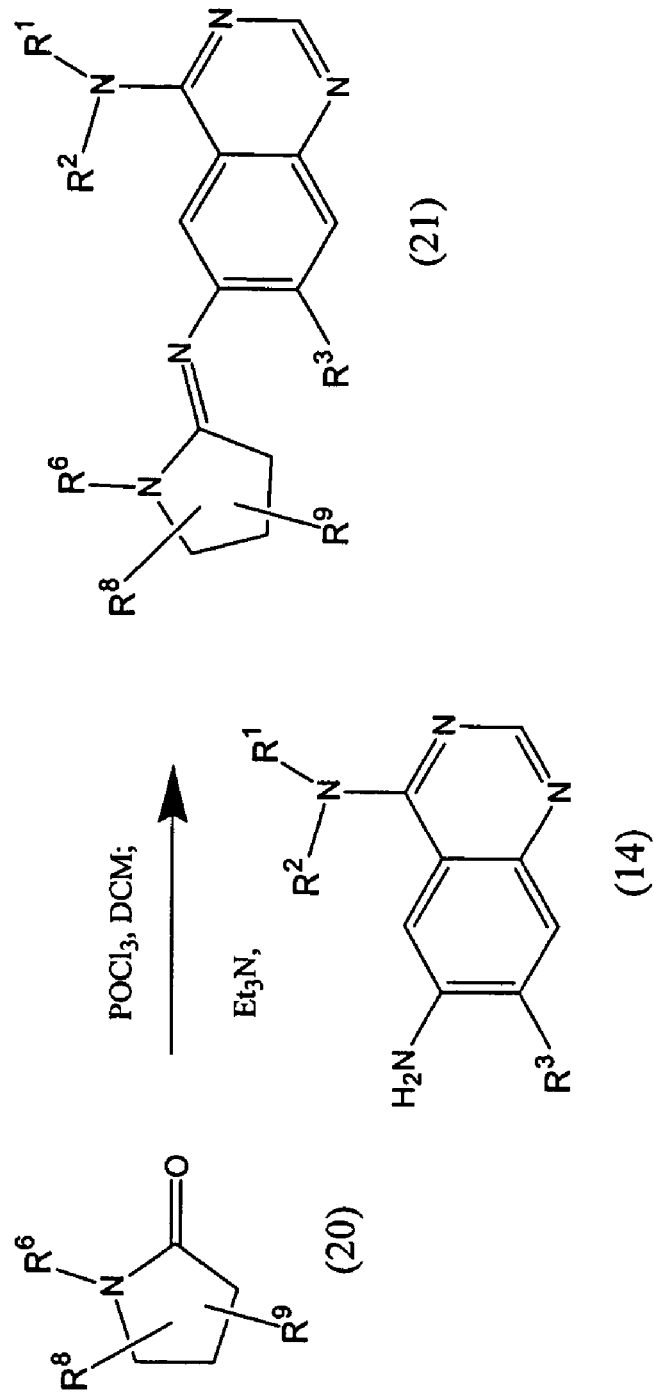
FIG. 5 shows a reaction scheme for the preparation of cyclic amidines.

FIG. 5 illustrates the synthesis of cyclic amidine compounds of the present invention. Cyclic amidines (21) can be prepared by treatment of aniline 14 with activated lactams (20) in suitable organic solvents such as PhMe, DCE, or DCM. Activation of lactams (20) can be accomplished by standard methods including but not limited to treatment with phosgene in PhMe and CHCl$_3$ at 0° C., triphosgene in PhMe at 0° C., and POCl$_3$ in DCM at −78° C. then warmed to room temperature. Most preferably, activation of lactams (20) is achieved by treatment with POCl$_3$ in DCM at −78° C. followed by warming to room temperature. Coupling can be achieved by the addition of aniline (14) to the activated lactam in the presence of amine base such as DIPEA, Et$_3$N, and pyridine. Preferably, the coupling is accomplished by the addition of aniline (14) to activated lactam in DCM at room temperature followed by the addition of Et$_3$N.

In order to illustrate the invention, the following examples are included. However, it is to be understood that these examples do not limit the invention and are only meant to suggest a method of practicing the invention. Persons skilled in the art will recognize that the chemical reactions described may be readily adapted to prepare a number of other quinazoline analogs of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

EXAMPLES

In the examples described below, unless otherwise indicated all temperatures are set forth in degrees Celsius. Reagents were purchased from commercial suppliers such as Aldrich Chemical Company, Lancaster, TCI or Maybridge, and were used without further purification unless otherwise indicated.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was done on a Biotage system (Manufacturer: Dyax Corporation) having a silica gel column or on a silica SepPak cartridge (Waters).

$^1$H-NMR spectra were recorded on a Varian instrument operating at 400 MHz. $^1$H-NMR spectra were obtained as CDCl$_3$ solutions (reported in ppm), using chloroform as the reference standard (7.25 ppm). Other NMR solvents were used as needed. When peak multiplicities are reported, the following abbreviations are used: s (singlet), d (doublet), t (triplet), m (multiplet), br (broadened), dd (doublet of doublets), dt (doublet of triplets).

Example 1

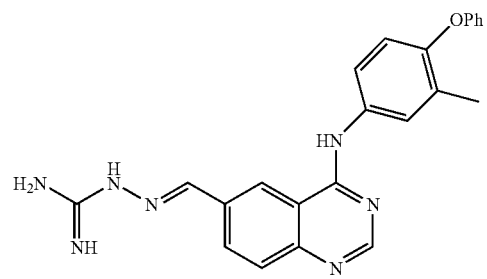

Preparation of (E)-4-(3-methyl-4-phenoxy-phenylamino)-quinazoline-6-carbaldehydeguanylhydrazone Step A: {2,3-Dihydroxy-3-[4-(3-methyl-4-phenoxy-phenylamino)-quinazolin-6-yl]-propyl}-carbamic acid tert-butyl ester is prepared by adding OsO$_4$ (0.8 mL of a 2.5% solution in tBuOH) to a stirred suspension of {3-[4-(3-methyl-4-phenoxy-phenylamino)-quinazolin-6-yl]-allyl}-carbamic acid tert-butyl ester (310 mg, 0.643 mmol) and NMO (97 mg, 0.83 mmol) in 5 ml 4:1 acetone:water. After stirring for 3 h, the reaction mixture is quenched by the addition of 5 ml 10% NaS$_2$O$_3$ solution and diluted with 10 ml DCM. The layers are separated and the aqueous layer is extracted with DCM. The combined organic layers are dried (Na$_2$SO$_4$) and concentrated to give the crude desired product. The product is used without further purification in Step B.

Step B: 4-(3-Methyl-4-phenoxy-phenylamino)-quinazoline-6-carbaldehyde is prepared by adding NaIO$_4$ (1.5 mL, 0.65 M in H$_2$O) to a slurry of silica gel (1 g) in DCM (6 mL) followed by the addition of {2,3-dihydroxy-3-[4-(3-methyl-4-phenoxy-phenylamino)-quinazolin-6-yl]-propyl}-carbamic acid tert-butyl ester (from Step A, ~0.64 mmol) in DCM (2 mL). The reaction mixture stirs for 1 hour, is filtered and washed with DCM (20 mL), and concentrated to give 280 mg of crude product. The product is used without further purification in Step E.

Step C: Hydrazinecarboxoimidothioic, methyl ester is prepared by adding MeI (6.1 g, 43 mmol) dropwise to hydrazine thiocarboxamide (4.5 g, 43 mmol) in EtOH (20 mL) at 60° C. The reaction mixture is stirred at 60° C. for one hour, and concentrated under reduced pressure. The residue is washed with diethyl ether (20 mL) and concentrated to yield 11 g of desired product, which is used without further purification.

Step D: Hydrazinecarboxoimidamide is prepared by stirring hydrazinecarboxoimidothioic, methyl ester (582 mg, 2.3 mmol), and NH$_3$ (2.8 mmol) in MeOH (1 mL), at reflux for 4 hours. The solvent is evaporated and the residual solid is used without further purification.

Step E: (E)-4-(3-Methyl-4-phenoxy-phenylamino)-quinazoline-6-carbaldehydeguanylhydrazone is prepared by stirring 4-(3-methyl-4-phenoxy-phenylamino)-quinazoline-6-carbaldehyde (39 mg, 0.11 mmol) in CH$_3$OH (2 mL), and adding hydrazinecarboximidamide (12 mg, 0.17 mmol) followed by 1 drop of concentrated HCl. After stirring the reaction mixture overnight, it is concentrated and purified by column chromatography (10:1:1 EtOAc:Hexanes: eOH) providing the desired product (31 mg, 68%). MS (ESI+) m/z 412 (M+1) detected.

Example 2

The following hydrazinecarboximidamides are prepared as described in Example 1, Step D using either hydrazinecarboxoimidothioic, methyl ester or methylhydrazinecarboximido-thioic acid, methyl ester and the appropriate amine.

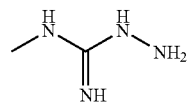

N-Methyl-hydrazinecarboximidamide

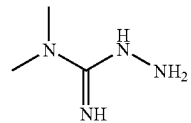

N,N-Dimethylhydrazine-carboximidamide

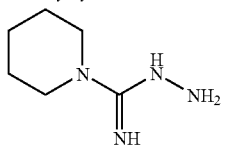

1-Piperidinecarboximidic acid hydrazide

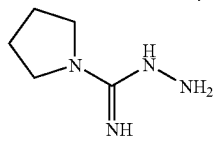

1-Pyrrolidinecarboximidic acid hydrazide

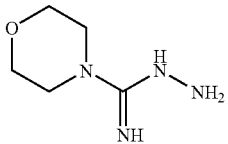

4-Morpholinecarboximidic acid hydrazide

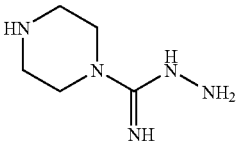

1-Piperazinecarboximidic acid hydrazide

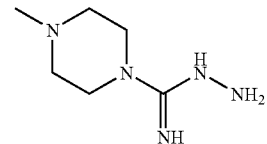

4-Methyl-piperazinecarboximidic acid hydrazide

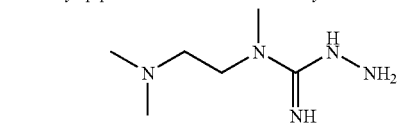

N-Methy-N-(2-dimethylamino-ethyl) hyrazinecarboximidamide

-continued

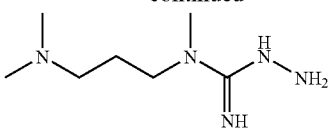

N-(3-Dimethylamino-propyl) hydrazinecarboximidamide

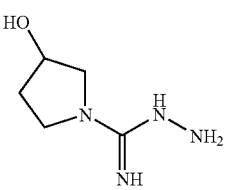

Pyrrolidin-3-ol-carboximidic acid hydrazide

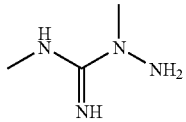

Methylaminecarboximidic acid, methylhydrazide

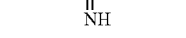

Dimethylaminecarboximidic acid, methylhydrazide

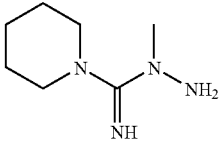

Piperidinecarboximidic acid, methylhydrazide

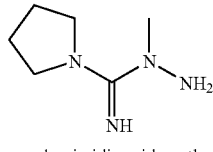

Pyrrolidine-carboximidic acid, methylhydrazide

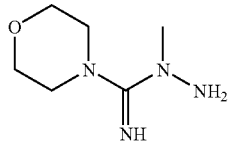

4-Morpholinecarboximidic acid, methylhydrazide

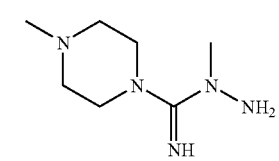

4-Methyl-piperazinecarboximidic acid, methylhydrazide

-continued

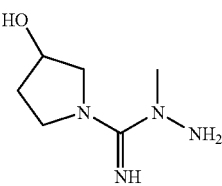

Pyrrolidin-3-ol-carboximidic acid, methylhydrazide

The following compounds (Examples 3-15) are prepared as described in Example 1, Step E using 4-(3-methyl-4-phenoxy-phenylamino)-quinazoline-6-carbaldehyde or 4-[3-chloro-4-(3-fluoro-benzyloxy)-phenylamino]-quinazoline-6-carbaldehyde and the appropriate hydrazinecarboximidamide.

Example 3

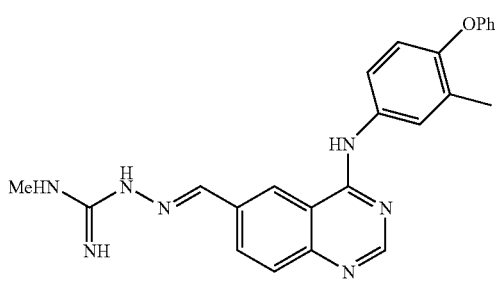

Preparation of (E)-N-Methyl-2-((4-(3-methyl-4-phenoxy-phenylamino))-6-quinazolinylmethalene)-hydrazinecarboximidamide MS (ESI+) m/z 426 (M+1) detected.

Example 4

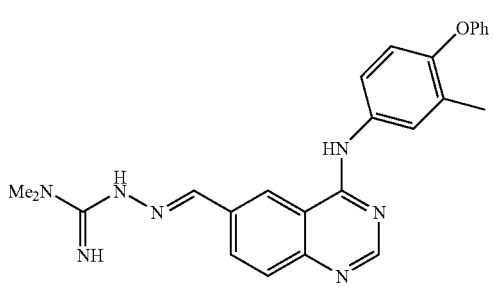

Preparation of (E)-N,N-Dimethyl-2-((4-(3-methyl-4-phenoxy-phenylamino))-6-quinazolinylmethylene)-hydrazinecarboximidamide MS (ESI+) m/z 440 (M+1) detected; $^1$H NMR (400 MHz, DMSO-d$_6$) δ 9.8 (s, 1 H), 8.63 (s, 1 H), 8.52 (s, 1 H), 8.3 (d,1H, J=8 Hz), 8.2 (s, 1 H), 7.8-7.6 (m, 3 H), 7.35 (t, 2 H, J=8 Hz), 7.05 (t, 1 H, J=8 Hz), 7.0 (t, 1 H, J=8 Hz), 6.85 (d, 2 H, J=8 Hz), 6.4 (br, 2 H), 2.96 (s, 6 H), 2.2 (s, 3 H).

Example 5

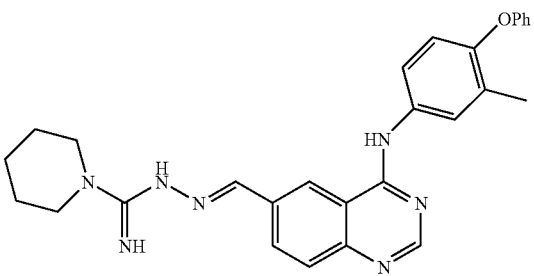

(E)-1-Piperidinecarboximidic acid, (2-((4-(3-methyl-4-phenoxy-phenylamino))-6-quinazolinylmethylene))hydrazide MS (ESI+) m/z 480 (M+1) detected.

Example 6

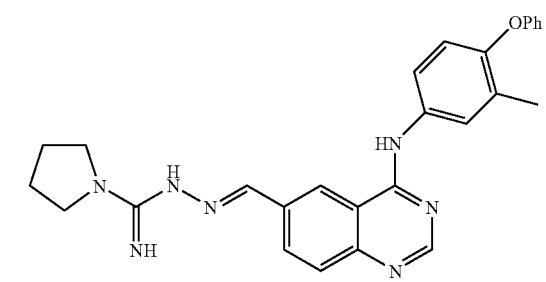

21

E)-1-Pyrrolidinecarboximidic acid, (2-((4-(3-methyl-4-phenoxy-phenylamino))-6-quinazolinylmethylene))hydrazide MS (ESI+) m/z 466 (M+1) detected.

Example 7

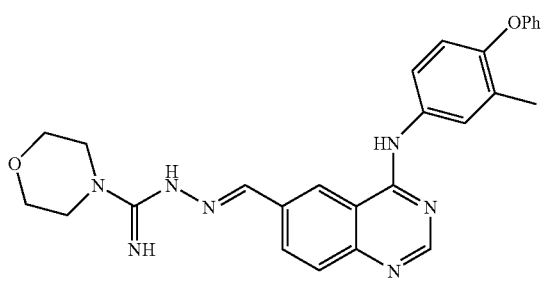

(E)-4-Morpholinecarboximidic acid, (2-((4-(3-methyl-4-phenoxy-phenylamino))-6-quinazolinylmethylene))hydrazide MS (ESI+) m/z 482 (M+1) detected.

Example 8

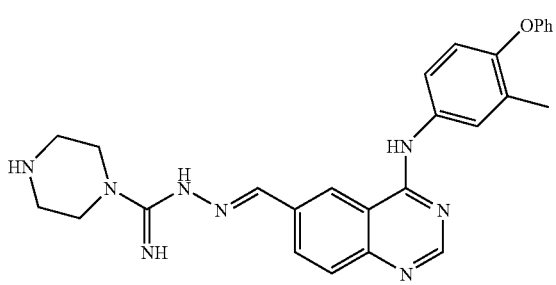

22

(E)-1-Piperazinecarboximidic acid, (2-((4-(3-methyl-4-phenoxy-phenylamino))-6-quinazolinylmethylene))hydrazide MS ESI (+) m/z 481 (M+1) detected; $^1$H NMR (400 MHz, DMSO-$d_6$) δ 9.8 (s, 1 H), 8.7 (s, 1 H), 8.56 (s, 1 H), 8.35 (d, 1 H, J=8 Hz), 8.2 (s, 1 H), 7.8 (s, 1 H), 7.72 (d, 2 H, J=8 Hz), 7.38 (t, 2 H, J=8 Hz), 7.08 (t, 1 H, J=8 Hz), 7.0 (d,, 1 H, J=8 Hz), 6.85 (d, 2 H, J=8 Hz), 6.4 (br, 2 H), 3.4 (br, 4 H), 2.75 (br, 4 H), 2.2 (s, 3 H).

Example 9

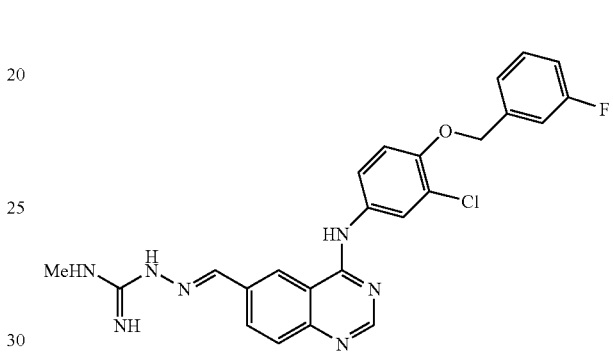

(E)-N-Methyl-2-((4-(3-chloro-4-(3-fluoro-phenoxy)-phenalamino))-6-quinazolinylmethylene)-hydrazinecarboximidamide Step A: (3-{4-[3-Chloro-4-(3-fluoro-benzyloxy)-phenylamino]-quinazolin-6-yl}-prop-2-ynyl)-carbamic acid tert-butyl ester is prepared by adding prop-2-ynyl-carbamic acid tert-butyl ester (0.978 g, 6.31 mmol), diisopropylamine (1.77 ml, 12.63 mmol), Pd(PPh$_3$)$_2$Cl$_2$ (210 mg, 0.30 mmol) and CuI (57 mg, 0.30 mmol) to a stirred solution of [3-chloro-4-(3-fluoro-benzyloxy)-phenyl]-(6-iodo-quinazolin-4-yl)-amine (3.11 g, 5.74 mmol) in THF (40 ml). After stirring the reaction mixture at rt under N$_2$ for 3 h, the THF is removed under reduced pressured and methylene chloride is added. The organic layer is washed with NH$_4$Cl (sat) and brine, and dried (Na$_2$SO4). The solvent is evaporated and the residual solid is used without further purification.

Step B: (3-{4-[3-Chloro-4-(3-fluoro-benzyloxy)-phenylamino]-quinazolin-6-yl}-allyl)-carbamic acid tert-butyl ester is prepared by adding (3-{4-[3-chloro-4-(3-fluoro-benzyloxy)-phenylamino]-quinazolin-6-yl}-prop-2-ynyl)-carbamic acid tert-butyl ester (3.00 g, 5.63 mmol) to a mixture of Red-Al (5 ml of a 65% wt solution in toluene) in THF (50 ml) at 0° C. under N$_2$. After stirring for 3 h at 0° C., the reaction mixture is quenched by the addition of 10 ml of 10% K$_2$CO$_3$ solution followed by water. The reaction mixture is extracted with ethyl acetate. The organic extracts are dried (Na$_2$SO$_4$), concentrated, and purified by column chromatography (EtOAc:Hex 1:1) to provide 2.01 g (67%) clean desired product.

Step C: (E)-N-Methyl-2-((4-(3-chloro-4-(3-fluoro-benzyloxy)-phenylamino))-6-quinazolinylmethylene)-hydrazinecarboximidamide is prepared by dissolving 4-[3-chloro-4-(3-fluoro-benzyloxy)-phenylamino]-quinazoline-6-carbaldehyde (prepared from (3-{4-[3-chloro-4-(3-fluoro-benzyloxy)-phenylamino]-quinazolin-6-yl}-allyl)-carbamic acid tert-butyl ester by the methods described in steps A and B of Example 1) (40 mg, 0.10 mmol) and N-methylhydrazine-carboximidamide (26.4 mg, 0.3 mmol) in MeOH (5 mL). Concentrated HCl (2 drops) is added, and the reaction mixture stirred overnight. The reaction mixture is concentrated and purified by column chromatography (EtOAc:Hex:MeOH:NH$_4$OH 9:1:1:1) providing (50-60% yield) of the desired product. MS APCI (+) m/z 478, 480 (M+1, Cl pattern) detected.

Example 10

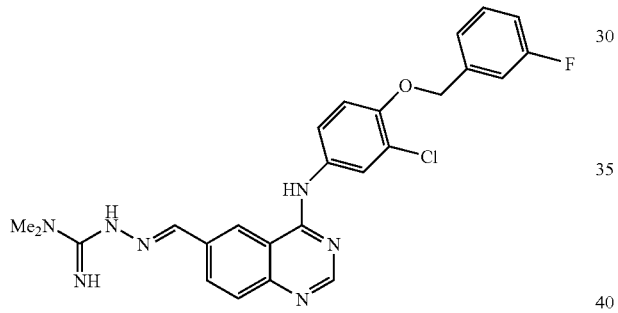

(E)-N,N-Dimethyl-2-((4-(3-chloro-4-(3-fluoro-phenoxy)-phenylamino))-6-quinazolinylmethylene)-hydrazinecarboximidamide MS (ESI+) m/z 492, 494 (M+1, Cl pattern) detected.

Example 11

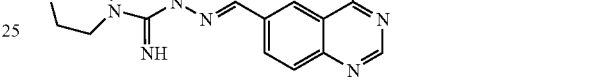

(E)-4-Morpholinecarboximidic acid, (2-((4-(3-chloro-4-(3-fluoro-phenoxy)-phenylamino))-6-quinazolinylmethylene))hydrazide MS APCI (+) m/z 534, 536 (M+1, Cl pattern) detected.

Example 12

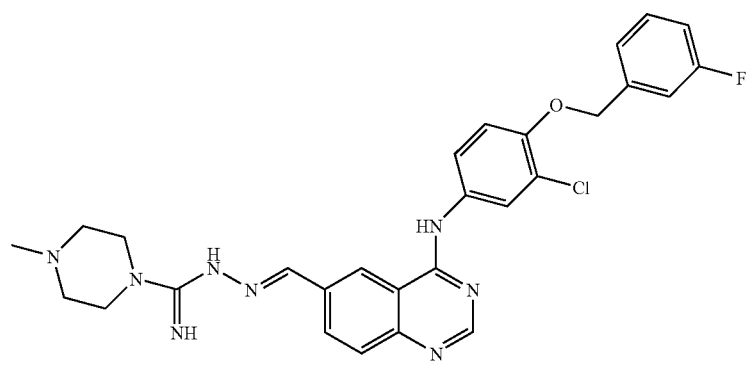

(E)-4-Methyl-piperazinecarboximidic acid (2-((4-(3-chloro-4-(3-fluoro-phenoxy)-phenylamino))-6-quinazolinylmethylene))hydrazide MS (ESI+) m/z 547, 549 (M+1, Cl pattern) detected.

Example 13

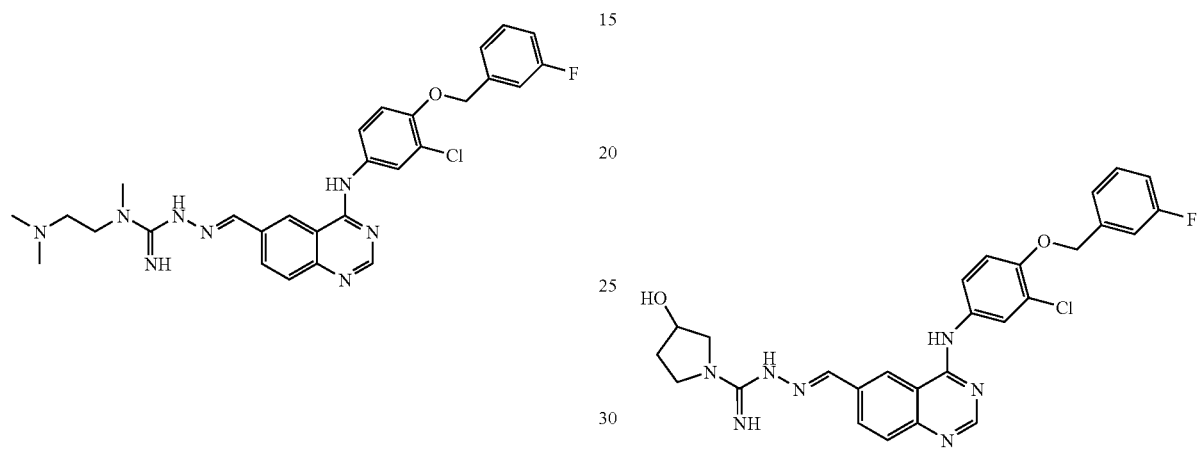

(E)-N-Methyl-N-(2-dimethylamino-ethyl)-2-((4-(3-chloro-4-(3-fluoro-phenoxy)-phenylamino))-6-quinazolinylmethylene)-Hydrazinecarboximidamide MS (ESI+) m/z 549, 551 (M+1, Cl pattern) detected.

Example 14

(E)-N-(3-Dimethylamino-propyl)-2-((4-(3-chloro-4-(3-fluoro-phenoxy)-phenylamino))-6-quinazolinylm-ethylene)-hydrazinecarboximidamide MS (ESI+) m/z 549, 551 (M+1, Cl pattern) detected.

Example 15

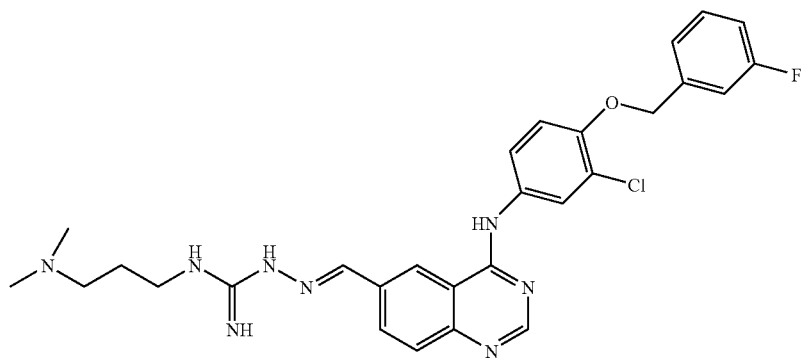

(E)-Pyrrolidin-3-ol-carboximidic acid (2-((4-(3-chloro-4-(3-fluoro-phenoxy)-phenalamino))-6-quinazolinylmethylene))hydrazide MS APCI (+) m/z 534, 536 (M+1, Cl pattern) detected.

Example 16

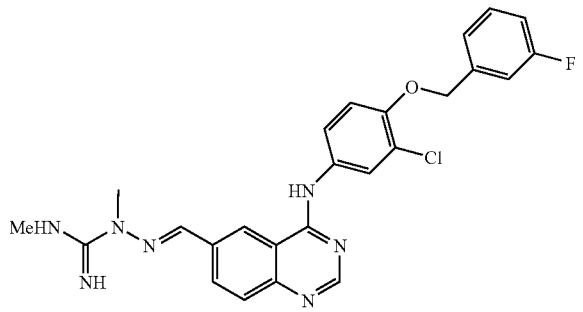

Preparation of (E)-Methylaminecarboximidic acid, (2-((4-(3-chloro-4-(3-fluoro-phenoxy)-phenylamino))-6-quinazolinylmethylene))-methylhydrazide (E)-Methylaminecarboximidic acid, (2-((4-(3-chloro-4-(3-fluoro-benzyloxy)-phenylamino))-6-quinazolinylmethylene))-methylhydrazide is prepared by dissolving 4-[3-chloro-4-(3-fluoro-benzyloxy)-phenylamino]-quinazoline-6-carbaldehyde (40 mg, 0.10 mmol) and methylaminecarboximidic acid, methylhydrazide (30.6 mg, 0.3 mmol) in DCM (2 mL) and IPA (1 mL). Glacial AcOH (4 drops) is added, and the reaction mixture stirred for 36 hrs. The reaction mixture is concentrated and purified by column chromatography (EtOAC:Hex:MeOH:NH$_4$OH 9:1:1: 1) providing (50-60% yield) of the desired product. MS (ESI+) m/z 492, 494 (M+1, Cl pattern) detected; $^1$H NMR (400 MHz, CD$_3$OD) δ 8.73( s, 1 H), 8.55 (s, 1 H), 8.47 (dd 1 H, J=8, 2 Hz), 8.24 (s, 1 H), 7.9 (d, 1 H, J=2 Hz), 7.82 (d, 1 H, J=8 Hz), 7.6 (dd 1 H, J=8, 2 Hz), 7.41 (m, 1 H), 7.31 (d, 1 H, J=8 Hz), 7.28 (d, 1 H, J=9 Hz), 7.18 (d, 1 H, J=8 Hz), 7.07 (m, 1 H), 5.24 (s, 2 H), 3.55 (s, 3 H), 3.07 (s, 3 H).

The following compounds (Examples 17-22) are prepared as described in Example 16 using 4-[3-chloro-4-(3-fluoro-benzyloxy)-phenylamino]-quinazoline-6-carbaldehyde and the appropriate aminecarboximidic acid, methylhydrazide.

Example 17

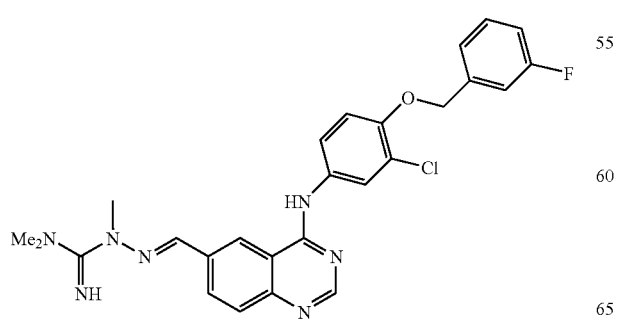

Example 18

(E)-Dimethylaminecarboximidic acid, (2-((4-(3-chloro-4-(3-fluoro-phenoxy)-phenylamino))-6-quinazolinylmethylene))-methylhydrazide MS (ESI+) m/z 506, 508 (M+1, Cl pattern) detected.

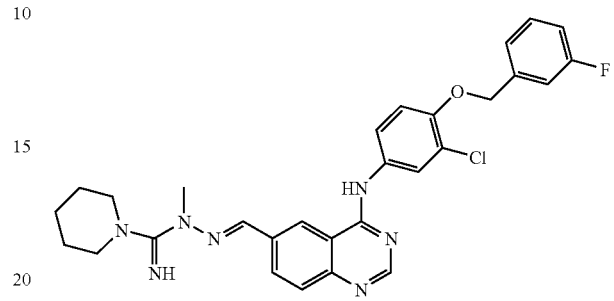

(E)-Piperidinecarboximidic acid, (2-((4-(3-chloro-4-(3-fluoro-phenoxy)-phenylamino))-6-quinazolinylmethylene))methylhydrazide MS (ESI+) m/z 546, 548 (M+1, Cl pattern) detected.

Example 19

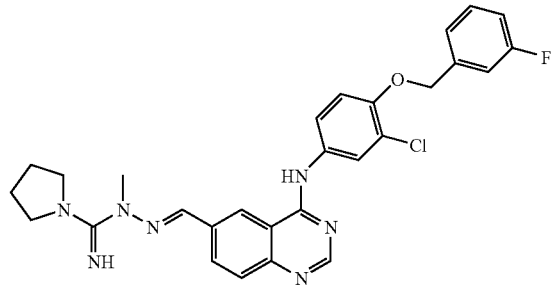

(E)-Pyrrolidine-carboximidic acid (2-((4-(3-chloro-4-(3-fluoro-phenoxy)-phenylamino))-6-quinazolinylmethylene))methylhydrazide MS (ESI+) m/z 532, 534 (M+1, Cl pattern) detected.

Example 20

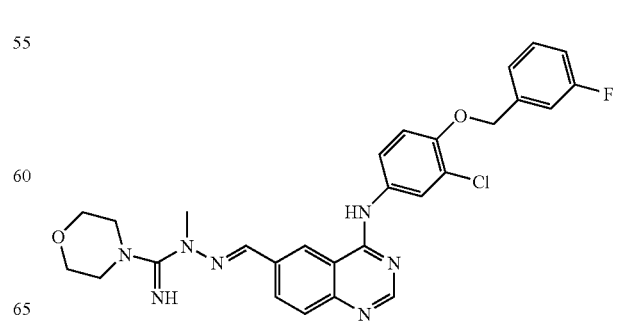

(E)-4-Morpholinecarboximidic acid, (2-((4-(3-chloro-4-(3-fluoro-phenoxy)-phenylamino))-6-quinazolinylmethylene))methylhydrazide MS (ESI+) m/z 548, 550 (M+1, Cl pattern) detected.

Example 21

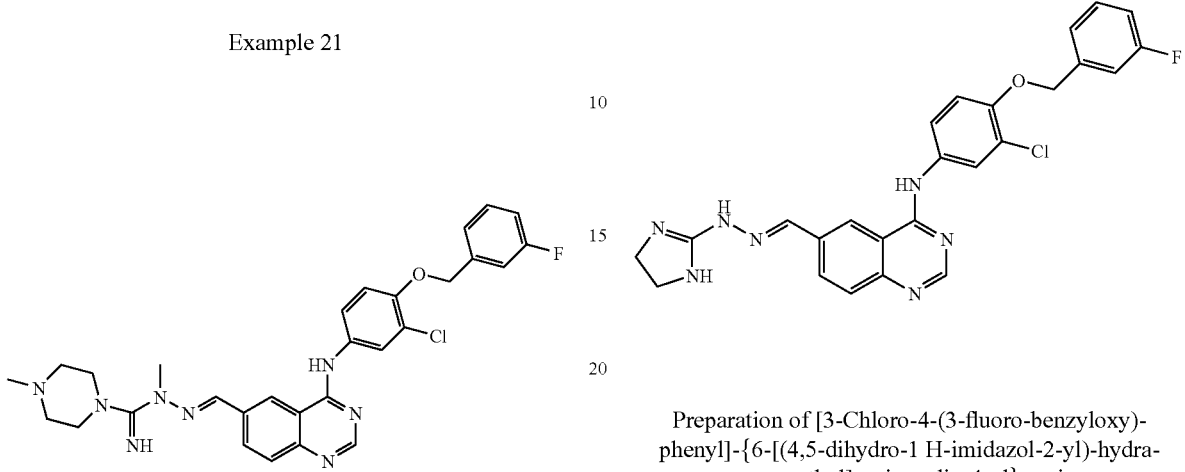

(E)-4-Methyl-piperazinecarboximidic acid (2-((4-(3-chloro-4-(3-fluoro-phenoxy)-phenylamino))-6-quinazolinylmethylene))methylhydrazide MS (ESI+) m/z 561, 563 (M+1, Cl pattern) detected.

Example 22

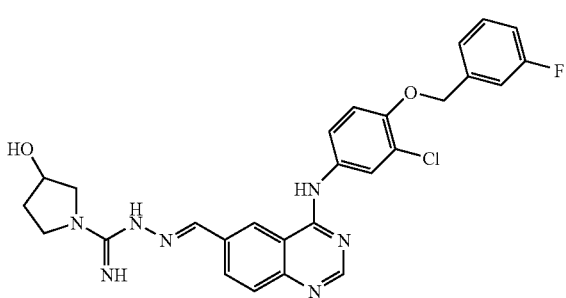

(E)-Pyrrolidin-3-ol-carboximidic acid, (2-((4-(3-chloro-4-(3-fluoro-phenoxy)-phenylamino))-6-quinazolinylmethylene))methylhydrazide MS (ESI+) m/z 548, 550 (M+1, Cl pattern) detected; $^1$H NMR (400 MHz, CD$_3$OD) 8.64(s, 1 H), 8.53 (s, 1 H), 8.35 (d 1 H, J=8 Hz), 8.17 (s, 1 H), 7.9 (d, 1 H, J=2 Hz), 7.83 (d, 1 H, J=8 Hz), 7.61 (dd 1 H, J=8, 2 Hz), 7.41 (m, 1 H), 7.31 (d, 1 H, J=8 Hz), 7.28 (d, 1 H, J=9 Hz), 7.18 (d, 1 H, J=8 Hz), 7.07 (td, 1 H, J=8, 3 Hz), 5.24 (s, 2 H), 4.51 (br, 1 H), 4.0 (m, 1 H), 3.92 (m, 1 H), 3.71 (m, 1 H), 3.55 (s, 3 H), 3.51 (m, 1 H), 3.36 (m, 1 H), 2.21 (m, 2 H).

Example 23

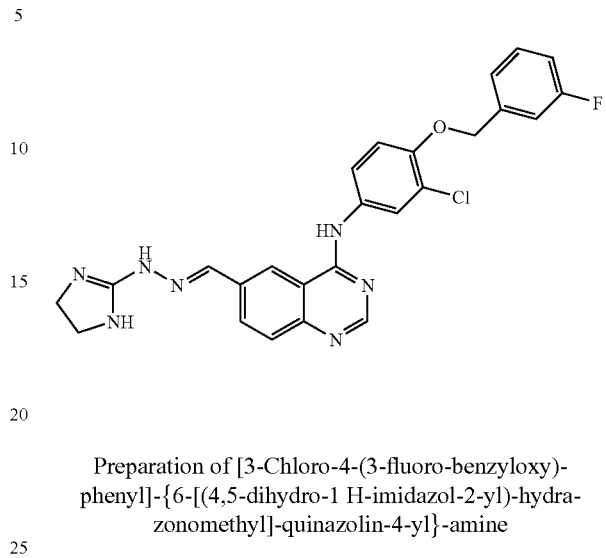

Preparation of [3-Chloro-4-(3-fluoro-benzyloxy)-phenyl]-{6-[(4,5-dihydro-1 H-imidazol-2-yl)-hydrazonomethyl]-quinazolin-4-yl}-amine Step A: 2-Methylsulfanyl-4,5-dihydro-1 H-imidazole is prepared by adding dropwise methyl iodide (2.4 g, 17 mmol) to a suspension of imidazolidine-2-thione (1.7 g, 16.9 mmol) in MeOH (10 mL) at 60° C. A clear solution results once the addition is complete. The reaction mixture is stirred for one hour and is concentrated to provide the desired product (4.0 g, 100% yield).

Step B: (4,5-Dihydro-1 H-imidazol-2-yl)-hydrazine is prepared by adding hydrazine (1 eq.) to 2-methylsulfanyl-4,5-dihydro-1 H-imidazole in EtOH (3 mL). The reaction is heated to 60° C. and stirred for 3 hours. The reaction mixture is concentrated to provide the desired product and used without further purification.

Step C: [3-Chloro-4-(3-fluoro-benzyloxy)-phenyl]-{6-[(4,5-dihydro-1 H-imidazol-2-yl)-hydrazonomethyl]-quinazolin-4-yl}-amine is prepared according to Example 16 using 4-[3-chloro-4-(3-fluoro-benzyloxy)-phenylamino]-quinazoline-6-carbaldehyde and (4,5-dihydro-1 H-imidazol-2-yl)-hydrazine providing (50-60% yield) of the desired product. MS (ESI+) m/z 490, 492 (M+1, Cl pattern) detected.

Example 24

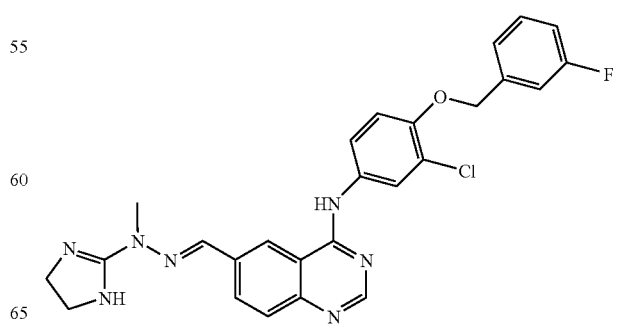

Preparation of [3-Chloro-4-(3-fluoro-benzyloxy)-phenyl]-{6-[(4,5-dihydro-1 H-imidazol-2-yl)-methyl-hydrazonomethyl]-quinazolin-4-yl}-amine Step A: N-(4,5-Dihydro-1 H-imidazol-2-yl)-N-methyl-hydrazine is prepared according to Step B of Example 23 using methyl hydrazine and 2-methylsulfanyl-4,5-dihydro-1 H-imidazole.

Step B: [3-Chloro4-(3-fluor-benzyloxy)-phenyl]-{6-[(4,5-dihydro-1 H-imidazol-2-yl)-methyl-hydrazonomethyl]-quinazolin-4yl}-amine is prepared according to Example 16 using 4-[3-chloro-4-(3-fluoro-benzyloxy)-phenylamino]-quinazoline-6-carbaldehyde and N-(4,5-dihydro-1 H-imidazol-2-yl)-N-methyl-hydrazine providing (50-60% yield) of the desired product. MS (ESI+) m/z 504, 506 (M+1, Cl pattern) detected; $^1$H NMR (400 MHz, CD$_3$OD) 8.58 (s, 1 H), 8.49 (s, 1 H), 8.29 (d 1 H, J=8 Hz), 7.88 (s, 1 H), 7.84 (s, 1 H), 7.76 (d, 1 H, J=8 Hz), 7.58 (d, 1 H, J=8 Hz), 7.41 (m, 1 H), 7.31 (d, 1 H, J=8 Hz), 7.28 (d, 1 H, J=9 Hz), 7.16 (d, 1 H, J=8 Hz), 7.06 (t, 1 H, J=8 Hz), 5.22 (s, 2 H), 3.71 (s, 4 H), 3.46 (s, 3 H).

Example 25

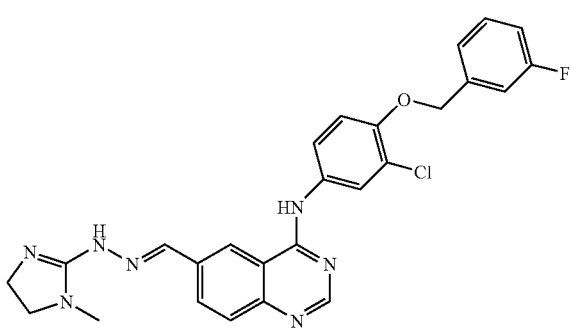

Preparation of [3-Chloro-4-(3-fluoro-benzyloxy)-phenyl]-{6-[(1-methyl-4,5-dihydro-1 H-imidazol-2-yl)-hydrazonomethyl]quinazolin-4-yl}-amine Step A: 1-Methyl-2-methylsulfanyl-4,5-dihydro-1 H imidazole is prepared by adding methyl iodide dropwise to 1-methyl-4,5-dihydro-1 H-imidazole-2-thiol in MeOH (5 mL) at 60° C. The reaction mixture is stirred at 60° C. for one hour and concentrated under reduced pressure. The residue is washed with Et$_2$O (20 ml) and concentrated to provide the desired product (2.21 g, 94% yield).

Step B: (1-Methyl-4,5-dihydro-1 H-imidazol-2-yl)-hydrazine is prepared by stirring together 1 methyl-2-methylsulfanyl-4,5-dihydro-1 H-imidazole (0.70 g, 2.7 mmol) and hydrazine (0.13 g, 2.7 mmol) in EtOH (5 ml) at 90° C. for 2 hours. The reaction mixture is concentrated under reduced pressure to provide the desired product (0.62 g, 94% yield), which is used without further purification.

Step C: [3-Chloro-4-(3-fluoro-benzyloxy)-phenyl]-{6-[(1-methyl-4,5-dihydro-1 H-imidazol-2-yl)-hydrzonomethyl]-quinazolin-4-yl}-amine is prepared according to Example 16 using 4-[3-chloro-4-(3-fluoro-benzyloxy)-phenylamino]-quinazoline-6- carbaldehyde and (1-methyl-4,5-dihydro-1 H-imidazol-2-yl)-hydrazine providing (62% yield) of the desired product. MS (ESI+) m/z 504 506 (M+1, Cl pattern) detected.

Example 26

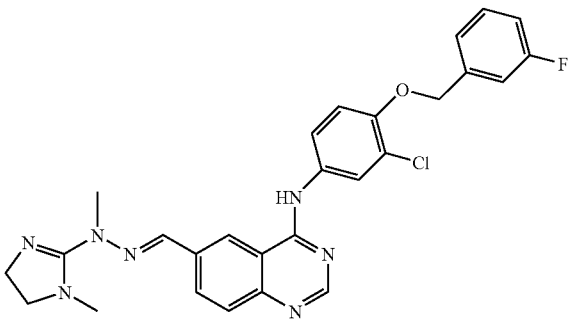

Preparation of [3-Chloro-4-(3-fluoro-benzyloxy)-phenyl]-{6-[methyl-(1-methyl-4,5-dihydro-1 H-imidazol-2-yl)-hydrazonomethyl]-quinazolin-4-yl}-amine Step A: N-Methyl-N-(1-methyl-4,5-dihydro-1 H-imidazol-2-yl)-hydrazine is prepared according to Step B of Example 25 using 1-methyl-2-methylsulfanyl-4,5-dihydro-1 H-imidazole and methyl hydrazine.

Step B: [3-Chloro-4-(3-fluoro-benzyloxy)-phenyl]-{6-[methyl(1-methyl-4,5-dihydro-1 H-imidazol-2-yl)-hydrazonomethyl]quinazolin-4-yl}-amine is prepared according to Example 15 using 4-[3-chloro-4-(3-fluoro-benzyloxy)-phenylamino]-quinazoline-6-carbaldehyde and N-methyl-N-(1-methyl-4,5-dihydro-1 H-imidazol-2-yl)-hydrazine providing (67% yield) of the desired product. MS (ESI+) m/z 518, 520 (M+1, Cl pattern) detected; $^1$H NMR (400 MHz, CD$_3$OD) 8.52 (s, 1 H), 8.51 (s, 1 H), 8.3 (d 1 H,J=8 Hz), 8.0 (s, 1 H), 7.91 (d, 1 H, J=2 Hz), 7.78 (d, 1 H, J=8 Hz), 7.61 (dd, 1 H, J=8, 2 Hz), 7.41 (m, 1 H), 7.31 (d, 1 H, J=8 Hz), 7.26 (d, 1 H, J=9 Hz), 7.16 (d, 1 H, J=8 Hz), 7.06 (t, 1 H, J=8 Hz), 5.22 (s, 2 H), 3.76 (s, 4 H), 3.49 (s, 3 H), 3.23 (s, 3 H).

The following compounds (Examples 27-30) are prepared as described in Example 16 using 4-[3-chloro-4-(3-fluoro-benzyloxy)-phenylamino]-7-methoxy-quinazoline-6-carbaldehyde and the appropriate imidazolyl-hydrazine.

Example 27

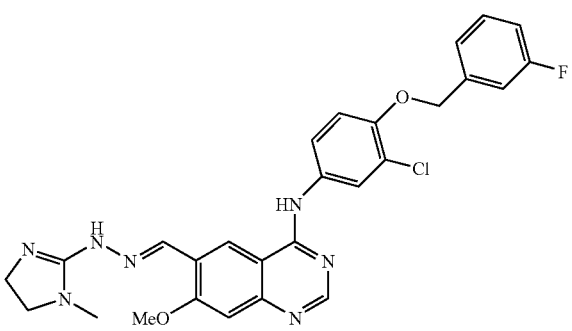

33

[3-Chloro-4-(3-fluoro-benzyloxy)-phenyl]-{7-methoxy-6-[(1-methyl-4,5-dihydro-1 H-imidazol-2-yl)-hydrazonomethyl]-quinazolin-4-yl}-amine MS (ESI+) m/z 534, 536 (M+1, Cl pattern) detected.

Example 28

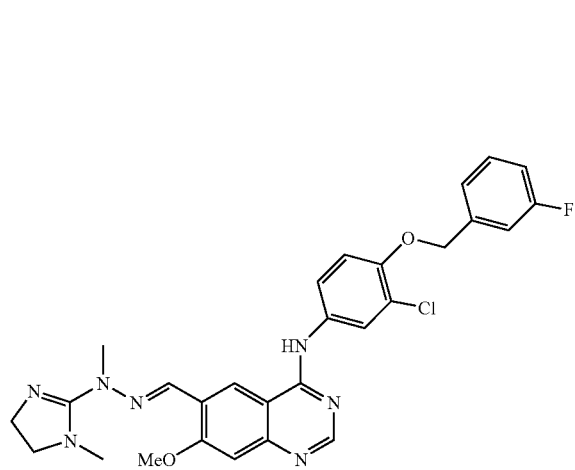

[3-Chloro-4-(3-fluoro-benzyloxy)-phenyl]-{7-methoxy-6-[methyl-(1-methyl-4,5-dihydro-1 H-imidazol-2-yl)-hydrazonomethyl]-quinazolin-4-yl}-amine MS (ESI+) m/z 548, 550 (M+1, Cl pattern) detected.

Example 29

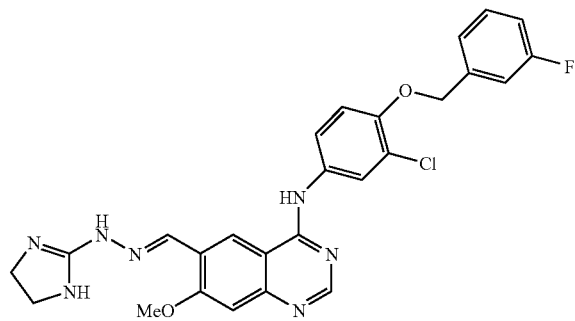

34

[3-Chloro-4-(3-fluoro-benzyloxy)-phenyl]-{6-[(4,5-dihydro-1 H-imidazol-2yl)-hydrazonomethyl]-7-methoxy-quinazolin-4-yl}-amine MS (ESI+) m/z 520, 522 (M+1, Cl pattern) detected.

Example 30

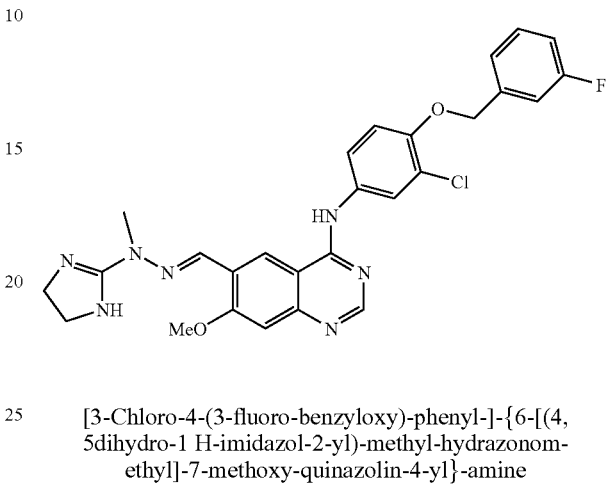

[3-Chloro-4-(3-fluoro-benzyloxy)-phenyl-]-{6-[(4,5dihydro-1 H-imidazol-2-yl)-methyl-hydrazonomethyl]-7-methoxy-quinazolin-4-yl}-amine MS (ESI+) m/z 534, 536 (M+1, Cl pattern) detected.

Example 31

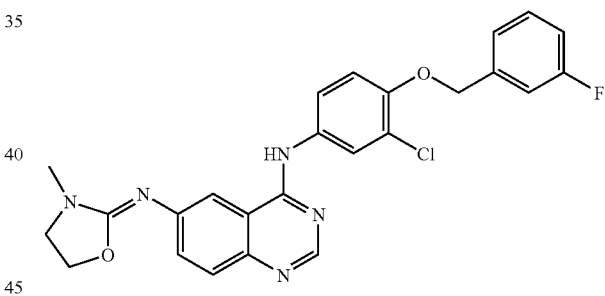

Preparation of N4-[3-Chloro-4-(3-fluoro-benzyloxy)-phenyl]-N6-(3-methyl-oxazolidin-2-ylidene)-quinazoline-4,6-diamine Step A: [3-Chloro-4-(3-fluoro-benzyloxy)-phenyl](6-nitro-quinazolin-4-yl)-amine HCl is prepared by stirring 3-chloro-4-(3-fluoro-benzyloxy)-phenylamime (1.0 g, 4.1 mmol) and 4-chloro-6-nitro-quinazoline (0. 1 g, 3.9 mmol) in DCE (10 mL) and t-BuOH (10 mL), under $N_2$ atmosphere at 80-90° C. for 19 hours. The reaction mixture is cooled, and the product isolated by filtration. Washing with DCM and drying yields the desired product (1.3 g, 73%).

Step B: N4-[3-Chloro-4-(3-fluoro-benzyloxy)-phenyl]-quinazoline-4,6-diamine is prepared by suspending [3-chloro-4-3-fluoro-benzyloxy)-phenyl]-(6-nitro-quinazolin-4-yl)-amine HCl (800 mg, 1.73 mmol) in MeOH (50 mL) and adding Pt/C (5%, wet) (700 mg). The flask is flushed with $N_2$, and NaOH (250 mg, 6.25 mmol) in water (6 mL) is added. The reaction mixture is stirred under 1 atmosphere $H_2$ and followed by LC/MS until completion. DCM is added and the reaction mixture is filtered through Celite. The Celite is washed with DCM and MeOH, and concentrated under N₂ atmosphere. The residue is immediately dissolved in DCM/EtOAc, dried with anhydrous Na₂SO₄, and concentrated, yielding 633 mg (92%) of desired product. The crude material is stored wider vacuum at room temperature.

Step C: N-4-[3-Chloro-4-(3-fluoro-benzyloxy)-phenyl] N6-(2-phenyl-N-cyano-isourea)-quinazoline-4,6-diamine is prepared by stirring N4-[3-chloro-4-(3-fluoro-benzyloxy)-phenyl]-quinazoline-4,6-diamine (0.63 g, 1.60 mmol) and diphenyl N-cyanocarbonimidate (1.0 g, 4.20 mmol), in THF (20 mL), DCE (10 mL) and t-BuOH (10 mL) at room temperature for 2 hours, then at 80-90° C. for 3 hours. An additional 0.40 g of diphenyl N-cyanocarbonimidate is added. After stirring at 80-90° C. for 3 hours, the reaction mixture is cooled to room temperature and concentrated. DCM (100 mL) is added, and the solid is isolated by filtration through a sintered glass funnel and dried, yielding 0.67 g (77.6%) of tan-yellow material.

Step D: N4-[-3-chloro-4-(3-fluoro-benzyloxy)-phenyl]-N6-(3-methyl-oxazolidin-2-ylidene)-quinazoline-4,6-diamine is prepared by dissolving N4-[3-chloro-4-(3-fluoro-benzyloxy)-phenyl]-N-6-(2-phenyl-N-cyano-isourea) quinazoline-4,6-diamine (10.4 mg, 0.02 mmol) and 2-methylamioethanol (6.0 mg, 0.08 mmol) in a 1:1 mixture of THF:i-PrOH (1 mL). The reaction mixture is stirred overnight at 80° C. The reaction mixture is concentrated and purified on a silica gel column (EtOAc-hexanes) yielding 3.6 mg (40%) of desired product. MS ESI (+) m/z 480, 478 (M+1, Cl pattern) detected; ¹H NMR (400 MHz, CD₃OD) δ 8.38 (s, 1 H), 7.85 (d, 1 H), 7.83 (d, 1 H), 7.55-7.65 (m, 4 H), 7.37-7.43 (m, 1 H), 7.23-7.31 (m, 2 H), 7.12 (d, 1 H), 7.05 (m, 1 H), 520 (s, 2 H), 4.41 (t, 2 H), 3.63 (t, 2 H), 3.01 (s, 3 H).

Using a process similar to that described in Step D of Example 31 with the appropriate amino alcohol, the following additional examples of compounds represented by Formula I are prepared:

Example 32

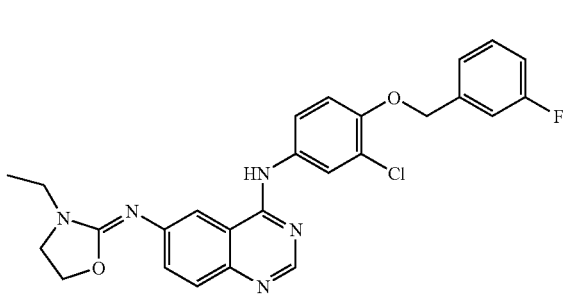

N-4-[3-Chloro-4-(3-fluoro-benzyloxy)-phenyl]-N6-(3-ethyl-oxazolidin-2-ylidene)-quinazoline-4,6-diamine MS ESI (+) m/z 494, 492 (M+1, Cl pattern) detected; ¹H NMR (400 MHz, CD₃OD) δ 8.38 (s, 1 H), 7.86 (d, 1 H), 7.84 (d, 1 H), 7.63-7.65 (m, 1 H), 7.55-7.60 (m, 3 H), 7.38-7.43 (m, 1 H), 7.24-7.31 (m, 2 H), 7.14 (d, 1 H), 7.05 (m, 1 H), 5.21 (s, 2 H), 4.41 (t, 2 H), 3.65 (t, 2 H), 3.48 (q, 2 H), 1.27 (t, 2 H).

Example 33

(2-{4-[3-Chloro-4-(3-fluoro-benzyloxy)-phenylamino]-quinazolin-6-ylimino}-3-methyl-oxazolidin-5-yl)-methanol MS ESI (+) m/z 510, 508 (M+1, Cl pattern) detected; ¹H NMR (400 MHz, CD₃OD) δ 8.41 (s, 1 H), 7.93 (d, 1 H), 7.87 (d, 1 H), 7.62-7.64 (m, 3 H), 7.40 (m, 1 H), 7.26-7.33 (m, 2 H), 7.16 (d, 1 H), 7.08 (m, 1 H), 5.22 (s, 2 H), 3.63-3.80 (m, 4 H), 3.48 (t, 3 H), 3.01 (d, 3 H), 0.90 (dd, 2 H).

Example 34

2-(2-{4-[3-Chloro-4-(3-fluoro-benzyloxy)-phenylamino]-quinazolin-6-ylimino}-oxazolidin-3-yl)-ethanol MS ESI (+) m/z 510, 508 (M+1, Cl pattern) detected; ¹H NMR (400 MHz, CD₃OD) δ 8.38 (s, 1 H), 7.86 (d, 1 H), 7.84 (d, 1 H), 7.65-7.55 (m, 4 H), 7.37-7.43 (m, 1 H), 7.24-7.31(m, 2 H), 7.14 (d, 1 H), 7.05 (m, 1 H), 5.21 (s, 2 H), 4.44 (t, 2 H), 3.84 (t, 2 H), 3.76 (t, 2 H), 3.55 (t, 2 H).

Example 35

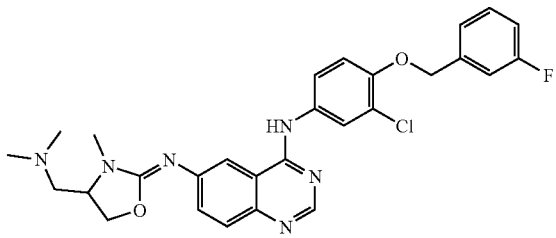

N-4-[3-Chloro-4-(3-fluoro-benzyloxy)-phenyl]-N6-(4-dimethylaminomethyl-3-methyl-oxazolidin-2-ylidene)-quinazoline-4,6-diamine 3-Dimethylamino-2-methylamino-propan-1-ol is prepared from 4-aza-DL-leucine 2 HCl. Di-tert-butyl dicarbonate (0.65 g, 2.97 mmol) is added to a biphasic mixture of 4-aza-DL-leucine 2 HCl (0.51 g, 2.47 mmol) in 10 ml 1:1 10% $Na_2CO_3$:MeCN. After stirring 16 hours, the MeCN is removed under reduced pressure and the aqueous layer is extracted with ethyl acetate. The aqueous layer is concentrated and purified by reverse phase column chromatography on a sep-pak C18 column (water) yielding 0.19 g (31%) 2-tert-butoxycarbonylamino-3-dimethylamino-propionic acid, sodium salt. The sodium salt is suspended in THF (5 ml) and cooled to 0° C. under $N_2$. LAH (3.8 ml of a 1.0 M solution in THF) is added and the reaction mixture warmed to rt and than to reflux. After stirring at reflux for 16 h, the reaction mixture is cooled to 0° C. and carefully quenched by the slow addition of $Na_2SO_4.10\ H_2O$. The reaction mixture is diluted with diethyl ether, warmed to room temperature and stirred for 30 min. The gray suspension is filtered through Celite and the filtrate concentrated to give 83 mg (82%) of 3-dimethylamino-2-methylamino-propan-1ol as an oil.

Analysis of the tituar product shows MS APCI (+) m/z 535, 537 (M+1, Cl pattern) detected; $^1$H NMR (400 MHz, $CD_3OD$) δ 8.41 (s, 1 H), 7.88 (s, 1 H), 7.86 (d, 1 H), 7.60 (m, 2 H), 7.56 (dd, 1 H), 7.40 (m, 1 H), 7.30 (d, 1 H) 7.25 (d, 1 H), 7.14 (d, 1 H), 7.05 (dt, 1 H), 5.21 (s, 2 H), 4.55 (t, 1 H), 4.26 (dd, 1 H), 3.99 (m, 1 H), 3.05 (s, 3 H), 2.81 (dd, 1 H), 2.63 (dd, 1 H), 2.40 (s, 6 H).

Example 36

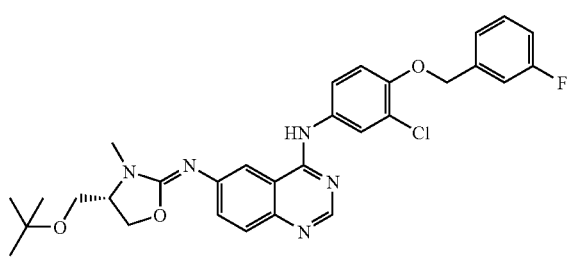

(S)-N6-(4-tert-Butoxymethyl-3-methyl-oxazolidin-2-ylidiene)-N4-[3-chloro-4-(3-fluoro-phenoxymethyl)-phenyl]-quinazoline-4,6-diamine N4-[3-Chloro-(3-fluoro-phenoxymethyl)-phenyl]-quinazoline-4,6-diamine is prepared from 3-chloro-(3-fluoro-phenoxymethyl)-phenylamine in a process similar to that described in Steps A and B, of Example 31.

(R)-3-tert-Butoxy-2-methylamino-propan-1-ol is prepared from Boc-O-tbutyl-(L)-serine. A THF solution (50 ml) of Boc-O-tbutyl-(L)-serine (1.90 g, 7.27 mmol) is slowly added to a stirred slurry of LAH (1.10 g, 29.1 mmol) in THF (50 ml) at room temperature. Upon completion of addition, the reaction mixture is heated to reflux and stirred for 17 hours. The reaction mixture is cooled to 0° C. and quenched by the slow addition of $Na_2SO_410H_2O$. Diethyl ether is added, and the slurry warmed to room temperature and stirred for 1 hour. The reaction mixture is filtered through Celite and the filtrate concentrated and purified on a silica gel column (2% MeOH in methylene chloride containing 2% $Et_3N$—increased to 20% MeOH) yielding 0.77 g (66%)(R)-3-tert-butoxy-2-methylamino-propan-1-ol.

Analysis of the titular product shows MS ESI (+) m/z 564, 566 (M+1, Cl pattern) detected; $^1$H NMR (400 MHz, $CDCl_3$) δ 8.7 (s, 1 H), 8.1 (s, 1 H), 7.8 (d, 1 H, J=9.4 Hz), 7.7 (dd, 1 H, J=9.4, 2.0 Hz), 7.6 (dd, 1 H, J=7.8, 2.0 Hz), 7.5 (m, 2 H), 7.4 (br s, 1 H), 7.2 (m, 1 H) 6.8-6.7 (m, 3 H), 5.1 (s, 2 H), 4.5 (t, 1 H, J=8.6 Hz), 4.2 (dd, 1 H, J=8.6, 5.5 Hz), 3.5 (A part of ABX, 1 H, $J_{AB}$=9.3 Hz, $J_{AX}$=4.3 Hz), 3.5 (B part of ABX, 1 H, $J_{AB}$=9.3 Hz, $J_{BX}$=5.5 Hz), 3.1 (s, 3 H), 1.2 (s, 9 H).

Example 37

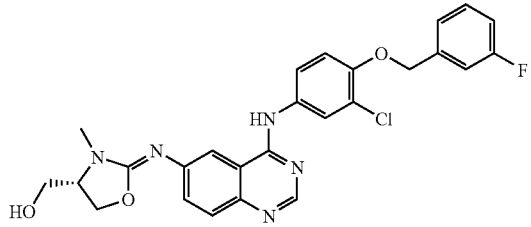

(S)-(2-{4-[3-Chloro-4-(3-fluoro-phenoxymethyl)-phenylamino]-quinazolin-6-ylimino}-3-methyl-oxazolidin-4-yl)-methanol (S)-(2-{4-[3-Chloro-4-(3-fluoro-phenoxymethyl)-phenylamino]-quinazolin-6-ylimino-}-3-methyl-oxazolidin-4-yl)-methanol is prepared from (S)-N6-(4-tert-butoxymethyl-3-methyl-oxazolidin-2-ylidene)-N4-[3-chloro-4-(3-fluoro-phenoxymethyl)-phenyl-]quinazoline-4,6-diamine. TFA (1 ml) is added to (S)-N6-(4-tert-butoxymethyl-3-methyl-oxazolidin-2-ylidene)-N4-[3-chloro-4-(3-fluoro-phenoxymethyl)-phenyl-]-quinazoline-4,6-diamine (0.104 g, 0.184 mmol) in 1 ml methylene chloride at 0° C. After stirring for 2 hours at 0° C. and 3 hours at room temperature, the reaction mixture is diluted with 1,2-dichloroethane and concentrated. The residue is diluted with methylene chloride and washed with 10% $Na_2CO_3$. The aqueous layer is extracted with methylene chloride, and the combined organic extracts dried ($Na_2SO_4$) and concentrated to give 60 mg (64%) pure desired product. MS ESI (+) m/z 508, 510 (M+1, Cl pattern) detected; $^1$H NMR (400 MHz, $CDCl_3$) δ 8.7 (s, 1 H), 8.1 (s, 1 H), 7.8-7.4 (m, 6 H), 7.2 (m, 1 H), 6.8-6.7 (m, 3 H), 5.1 (s, 2 H), 4.5 (m, 2 H), 4.0 (dd, 1 H, J=13, 3.9 Hz), 3.9 (m, 1 H), 3.8 (br d, 1 H, J=13.0 Hz), 3.1 (s, 3 H).

Example 38

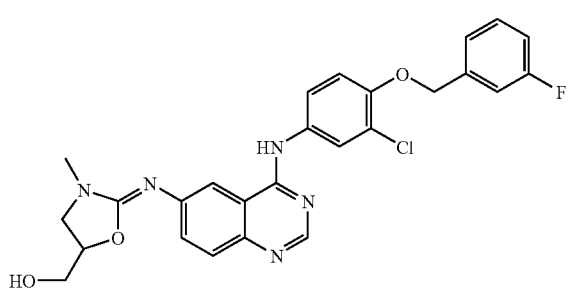

(2-{4-[3-Chloro-4-(3-fluoro-phenoxymethyl)-phenylamino]-quinazolin-6-ylimino}-3-methyl-oxazolidin-5-yl)-methanol MS ESI (+) m/z 508, 510 (M+1, Cl pattern) detected; $^1$H NMR (400 MHz, CD$_3$OD) δ 8.5 (s, 1 H), 8.1 (s, 1 H), 7.9 (s, 1 H), 7.8 (d, 1 H, J=8.6 Hz), 7.7 (m, 2 H), 7.5 (d, 1 H, J=7.8 Hz), 7.5 (m, 1 H) 6.8 (d, 1 H, J=7.8 Hz), 6.8 (d, 1 H, J=11.0), 6.7 (m, 1 H), 5.2 (s, 2 H), 4.7 (m, 1 H), 3.8 (A part of ABX, 1 H, J$_{AB}$=12.5 Hz, J$_{AX}$=2.5 Hz), 3.7-3.6 (m, 2 H) 3.5 (t, 1 H, J=7.0 Hz), 3.0 (s, 3 H).

Example 39

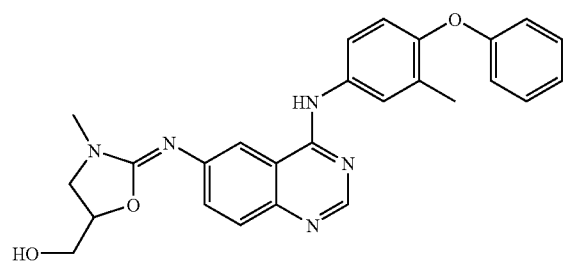

{3-Methyl-2-[4-(3-methyl-4-phenoxy-phenylamino)-quinazolin-6-ylimino]-oxazolidin-5-yl}-methanol N4-(3-Methyl-4-phenoxy-phenyl)-quinazoline-4,6-diamine is prepared from 3-methyl-4-phenoxy-phenylamine similar to the process described in Steps A and B of Example 31.

Product analysis of the titular product shows MS ESI (+) m/z 456 (M+1) detected; $^1$H NMR (400 MHz, DMSO-d$_6$) δ 9.5 (s, 1 H), 8.5 (s, 1 H), 8.0 (s, 1 H), 7.9 (s, 1 H), 7.8 (d, 1 H), 7.6 (m, 2 H), 7.4 (t, 2 H), 7.1 (t, 1 H), 7.0 (d, 1 H), 6.9 (d, 2 H), 5.1 (m, 1 H), 4.7 (br, 1 H), 3.6 (m, 2 H), 3.5 (m, 1 H), 3.4 (m, 1 H), 2.9 (s, 3 H), 2.2 (s, 3 H).

Example 40

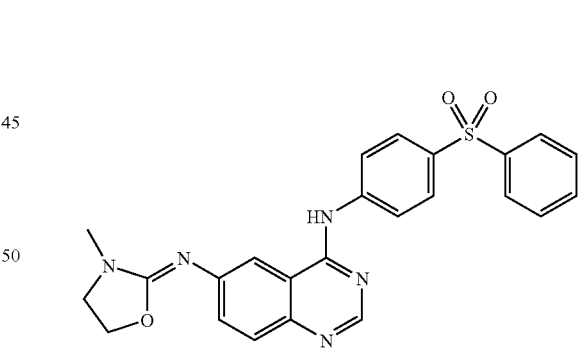

(2-{4-[3-Chloro-4-(6-methyl-pyridin-3-yloxy)-phenylamino]-quinazolin-6-ylimino}-3-methyl-oxazolidin-5-yl)-methanol N4-[3-Chloro-4-(6-methyl-pyridin-3-yloxy)-phenyl]-quinazoline-4,6-diamine is prepared from 3-chloro-4-(6-methyl-pyridin-3-yloxy)-phenylamine similar to the process described in Steps A and B of Example 31.

Product analysis of the titular product shows MS ESI (+) m/z 491 (M+1) detected; $^1$H NMR (400 MHz, DMSO-d$_6$) δ 9.7 (s, 1 H), 8.5 (s, 1 H), 8.4 (s, 1 H), 8.2 (s, 1 H), 7.9 (m, 2 H), 7.6 (m, 2 H), 7.2 (m, 3 H), 5.1 (m, 1 H), 4.7 (br, 1 H), 3.6 (m, 2 H), 3.5 (m, 1 H), 3.4 (m, 1 H), 2.9 (s, 3 H), 2.5 (s, 3 H).

Example 41

N4-(4-Benzenesulfonyl-phenyl)-N6-(3-methyl-oxazolidin-2-ylidene)-quinazoline-4,6-diamine N4-(4-Benzenesulfonyl-phenyl)-quinazoline-4,6-diamine is prepared from 4-benzenesulfonyl-phenylamine similar to the process described in Steps A and B of Example 31.

Product analysis of the titular product shows MS ESI (+) m/z 460 (M+1) detected; $^1$H NMR (400 MHz, CD$_3$OD) δ

8.52 (s, 1 H), 8.12 (d, 2 H), 7.96 (m, 4 H), 7.89 (d, 1 H), 7.44-7.70 (m, 5 H), 4.43 (t, 2 H), 3.64 (t, 2 H), 3.02 (s, 1 H).

Example 42

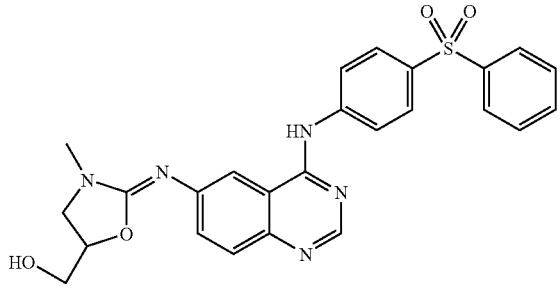

{2-[4-(4-Benzenesulfonyl-phenylamino)-quinazolin-6-ylimino]-3-methyl-oxazolidin-5-yl}-methanol MS ESI (+) m/z 490 (M+1) detected; $^1$H N (400 MHz, CD$_3$OD) δ 8.53 (s, 1 H) 8.16 (d, 2 H), 7.94-7.99 (m, 5 H), 7.58-7.69 (m, 5 H), 3.62-3.79 (m, 4 H), 3.46-3.51 (m, 1 H), 3.01 (d, 3 H).

Example 43

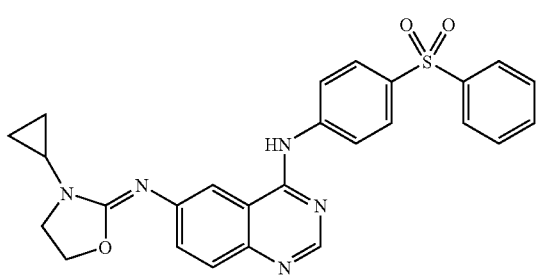

N4-(4-Benzenesulfonyl-phenyl)-N6-(3-cyclopropyl-oxazolidin-2-ylidene)-quinazoline-4,6-diamine 2-Cyclopropylamino ethanol can be prepared by LAH reduction of the corresponding ethyl oxalamide (Morrow, D. F. et at *J Med Chem* 1973, 16(6), 736-739).

Product analysis of the titular product shows MS ESI (+) m/z 486 (M+1) detected; $^1$H NMR (400 MHz, CDCl$_3$) δ 8.7 (s, 1H), 8.0 (m, 6H), 7.8 (d, 1 H, J=8.6 Hz), 7.7-7.5 (m, 6H), 4.4 (t, 2 H, J=7.2 Hz), 3.6 (t, 2 H, J=7.2 Hz), 2.6 (m, 1 H), 0.89-0.82 (m, 4 H).

Example 44

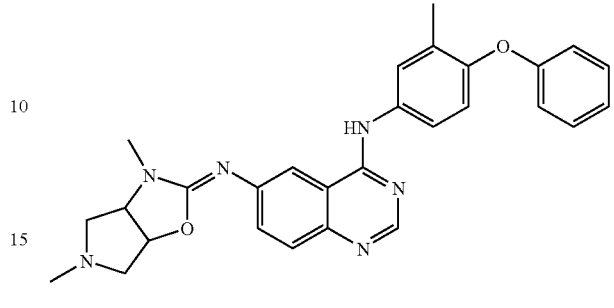

N6-(Dimethyl-hexahydro-pyrrolo[3,4]-doxazol-2-ylidene)-N4-(3-methyl-4-phenoxyphenyl)-quinazoline-4,6-diamine 1-Methyl-4-methylamino-pyrrolidin-3-ol is prepared in three steps from 3-pyrroline. Di-tert-butyl dicarbonate (25 g, 113 mmol) is added to a stirred solution of 3-pyrroline (65% pure—remainder pyrrolidine, 7.1 g, 103 mmol) in methylene chloride (50 ml) at 0° C. The reaction mixture is warmed to room temperature, stirred for 1 hour, and concentrated to give 17.1 g 2,5-dihydro-pyrrole-1-carboxylic acid tert-butyl ester contaminated with 5% di-tert-butyl dicarbonate.

N-Propanol (20 ml), benzylcarbamate (4 g, 27 mmol), and 1,3-dichloro-5,5-dimethylhydantoin (2.6 g, 13 mmol) are added to a solution of NaOH (1 g, 27 mmol) in water (40 ml). The reaction mixture is cooled to 0° C. and a solution of 2,5-dihydro-pyrrole-1-carboxylic acid tert-butyl ester (1.51 g, 8.92 mmol) in n-propanol (10 ml) is added. A solution of potassium osmate (0.098 g, 0.268 mmol) in 0.65 M NaOH (1 ml) is added. The reaction mixture is stirred at 0° C. for 1 hour and then at room temperature for 2 hours. The reaction mixture is quenched with sodium sulfite (1.90 g, 15 mmol) and diluted with approximately 1:1 EtOAc:water (100 ml). The aqueous layer is extracted with ethyl acetate, the combined organic extracts dried (MgSO$_4$) and concentrated. Purification on a silica gel column (4:1 hexanes:EtOAc) yields 3-benzyloxycarbonylamino-4-hydroxy-pyrrolidine-1-carboxylic acid tert-butyl ester.

LAH (1.40 g, 35.0 mmol) is slowly added to a stirred solution of 3-benzyloxycarbonylamino-4-hydroxy-pyrrolidine-1-carboxylic acid tert-butyl ester in THF (15 ml) at room temperature. The reaction mixture is heated to reflux under N$_2$ for 2 hours and then cooled to 0° C. The reaction mixture is quenched by the slow addition of Na$_2$SO$_4$.10 H$_2$O, warmed to room temperature, diluted with ethyl acetate and filtered through Celite. The filtrate is concentrated and purified on a silica gel column (10:1:0.5 methylene chloride, MeOH, 30% NH$_4$OH solution) to yield 0.21 g (18% for two steps) 1-methyl-4-methylamino-pyrrolidin-3-ol.

Product analysis of the titular product shows MS APCI (+) m/z 481 (M+1) detected; $^1$H NMR (400 MHz, CD$_3$OD) δ 8.37 (s, 1 H), 7.86 (s, 1 H), 7.64 (s, 2 H), 7.60 (d, 1 H), 7.51 (dd, 1 H), 7.31 (t, 2 H), 7.04 (t, 1 H), 6.93 (t, 3 H), 5.12 (dd, 1

H), 4.33 (dd, 1 H), 3.20 (m, 2 H), 3.03 (s, 3 H), 2.38 (s, 3 H), 2.27 (dd, 1 H), 2.23 (s, 3 H), 2.16 (dd, 1 H).

Example 45

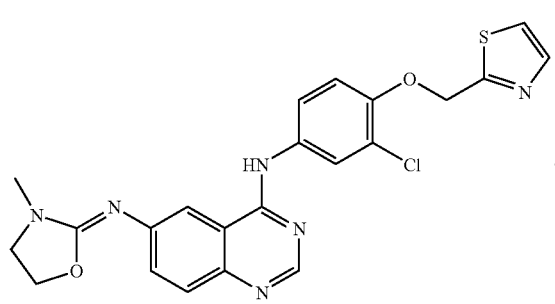

N4-[3-Chloro-4-(thiazol-2-ylmethoxy)-phenyl]-N6-(3-methyl-oxazolidin-2-ylidene)-quinazoline-4,6-diamine 3-Chloro-4-(thiazol-2-ylmethoxy)-phenylamine is prepared in three steps from thiazole-2-carbaldehyde. Sodium borohydride (16.0 g, 415 mmol) is added to a stirred solution of thiazole-2-carbaldehyde (24.2 g, 214 mmol) in MeOH (400 ml) at 0° C. The reaction mixture is warmed to room temperature. After 1 h, the reaction mixture is quenched by the addition of water and the organics are removed by concentration. The resulting aqueous mixture is extracted with EtOAc. The combined organic extracts are dried (Na$_2$SO$_4$) and concentrated to give thiazol-2-yl-methanol (24.0 g, 100%).

2-(2-Chloro-4-nitro-phenoxymethyl)-thiazole is prepared by adding thiazol-2-yl-methanol (2.74 g, 23.76 mmol) to a slurry of sodium hydride (1.21 g of a 60% dispersion in oil, 30.2 mmol) in DMF (10 ml) at 0° C. After several minutes, 2-chloro-1-fluoro-4-nitro-benzene (3.79 g, 21.60 mmol) is added and the reaction mixture warmed to room temperature. The reaction mixture is stirred at room temperature for 3 h, and 60° C. for 16 h. After cooling to room temperature, the reaction mixture is poured into 200 ml water. The resulting precipitate is collected by filtration, washed with water, and dried in vacuo to give 2-(2-chloro-4-nitrophenoxymethyl)-thiazole (5.80 g, 99%) which is used without further purification.

3-Chloro-4-(thiazol-2-ylmethoxy)-phenylamine is prepared by added Zn dust (55.9 g, 856 mmol) to a mixture of 2-(2-chloro-4-nitro-phenoxymethyl)-thiazole (47.0 g, 190 mmol) in 5:1 MeOH:saturated aqueous NH4Cl solution (600 ml). After 2 h, the reaction mixture is filtered, and the filtrate concentrated. The resulting solid is triturated with water to give 3-chloro-4 thiazol-2-ylmethoxy)-phenylamine (35.2 g, 85%).

N4-[3-Chloro-4-(thiazol-2-ylmethoxy)-phenyl]-quinazoline-4,6-diamine is prepared from 3-chloro-4-(thiazol-2-ylmethoxy)-phenylamine similar to the process described in Steps A and B of Example 31.

Product analysis of the titular product shows MS ESI (+) m/z 467 (M+1) detected; $^1$H NMR (400 MHz, DMSO-d$_6$) δ 9.5 (s, 1 H), 8.4 (s, 1 H), 8.1 (m, 1 H), 7.9 (d, 1 H), 7.8 (m, 1 H), 7.8 (d, 1 H), 7.8 (m, 1 H), 7.6 (d, 1 H), 7.5 (dd, IR), 7.3 (d, 1 H), 5.5 (s, 2 H), 4.4 (t, 2 H), 3.6 (t, 2 H), 2.9 (s, 3 H).

Example 46

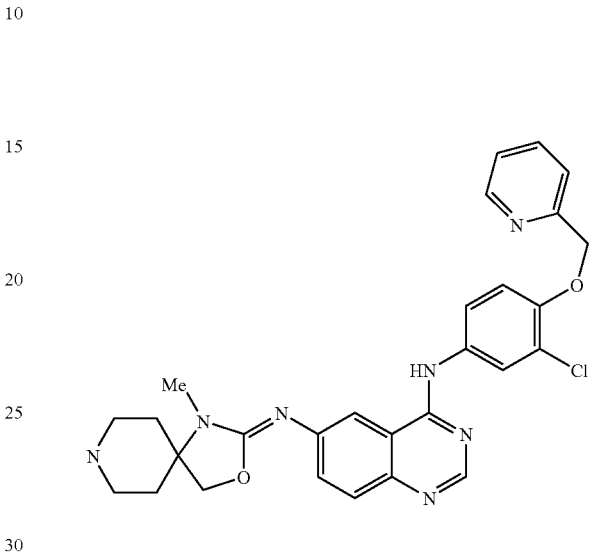

N4-[3-Chloro-4-(pyridin-2-ylmethoxy)-phenyl]-N6-(dimethyl-3-oxa-1,8-diaza-spiro[4,5]dec-2-ylidene)-quinazoline-4,6-diamine (1-Methyl-4-methylamino-piperidin-4-yl)-methanol is prepared from 4-amino-piperidine-4-carboxylic acid 2 HCl. Methyl chloroformate (0.40 g, 4.2 mmol) is added dropwise to a mixture of 4-amino-piperidine-4-carboxylic acid 2 HCl (0.278 g, 1.28 mmol) and Et$_3$N (0.713 g, 7.04 mmol) in THF (10 ml) at room temperature. After 16 h, the reaction mixture is filtered, rinsed with EtOAc and concentrated. A solution of LAH in THF (5 ml of a 1 M solution) is added to the residue. After stirring at reflux for 4 h, the reaction mixture is cooled to 0° C. and carefully quenched with Na$_2$SO$_4$.10H$_2$O. After warming to room temperature the reaction mixture is diluted with EtOAc and filtered through Celite. The filtrate is concentrated to give (1-methyl-4-methylamino-piperidin-4-yl)-methanol which is carried forward without purification.

N4-[3-Chloro-4-(pyridin-2-ylmethoxy)-phenyl]-quinazoline-4,6-diamine is prepared from 3-chloro-4-(pyridin-2-ylmethoxy)-phenylamine similar to the process described in Steps A and B of Example 31.

Product analysis of the titular product shows MS ESI (+) m/z 544 (M+1) detected; $^1$H NMR (400 MHz, CD$_3$OD) 8.56 (d, 1 H, J=5 Hz), 8.46-8.44 (m, 2 H), 8.07 (d, 1 H, J=2 Hz), 7.93-7.89 (m, 2 H), 7.74 (d, 1 H, J=9.2 Hz), 7.72 (d, 1 H, J=8 Hz), 7.63 (dd, 1 H, J=8.8, 2.4 Hz), 7.4 (t, 1 H, J=6.4 Hz), 7.17 (d, 1 H, J=8.8 Hz), 5.28 (s, 2 H), 3.98 (s, 2 H), 3.24 (m, 2 H), 2.88 (s, 3 H), 2.71 (m, 2 H), 2.60 (s, 3 H), 2.29 (td, 2 H, J=13, 3.6 Hz), 1.76 (d, 2 H, J=13.6 Hz).

Example 47

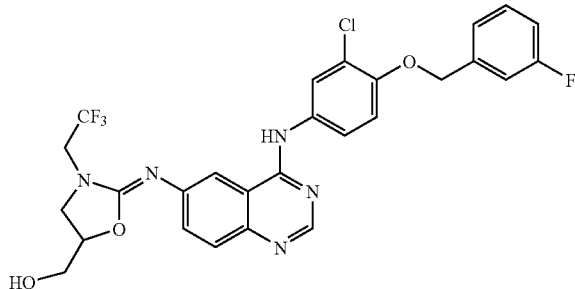

[2-{4-[3-Chloro-4-(3-fluoro-benzyloxy)-phenylamino]-quinazolin-6-ylimino}-3-(2,2,2,-trifluoroethyl)-oxazolidin-5-yl]-methanol 3-(2,2,2-Trifluoro-ethylamino)-propane-1,2-diol is prepared by adding a MeOH (80 ml) solution of 2,2,2-trifluoro-ethylamine (10.83 g, 109.3 mmol) dropwise to a solution of glycidol (3.00 g, 40.50 mmol) in MeOH (20 ml) at 0° C. The reaction mixture is warmed to room temperature, stirred for 16 h and concentrated. Purification on a silica gel column (9:1 EtOAc:hexanes) gives the desired product as a colorless oil (2.05 g, 33%).

[2-{4-[3-Chloro-4-(3-fluoro-benzyloxy)-phenylamino]-quinazolin-6-ylimino}-3-(2,2,2-trifluoro-ethyl)-oxazolidin-5-yl]-methanol is prepared from N4-[3-chloro-4-(3-fluoro-benzyloxy)-phenyl]-quinazoline-4,6-diamine. 1,1-Thiocarbonyldiimidazole (55 mg, 0.28 mmol) is added to a solution of N4-[3-chloro-4-(3-fluoro-benzyloxy)-phenyl]-quinazoline-4,6-diamine (100 mg, 0.253 mmol) in 1:1 THF:DCE (1 ml). After 30 min, a 1:1 THF:DCE (1 ml) solution of 3-(2,2,2-trifluoro-ethylamino)-propane-1,2-diol (88 mg, 0.51 mmol) is added. After 16 h, the reaction mixture is concentrated and the resulting solid is suspended in Et$_2$O and filtered. EDCI (110 mg, 0.560 mmol) and catalytic DMAP is added to a suspension of the solid thiourea in 1:1 THF:DCE (4 ml), After 6 h, an additional 200 mg EDCI is added and the reaction mixture is heated to 70° C. After 16 h, the reaction mixture is cooled to room temperature and diluted with water. The aqueous layer is extracted with EtOAc. The combined organic extracts are dried (Na$_2$SO$_4$) and concentrated. Purification on a silica gel column (EtOAc) yields the desired product as a yellow solid (10 mg, 7%0). MS ESI (+) m/z 576.2, 578.2 (M+1) detected; $^1$H NMR (400 MHz, DMSO-d$_4$) δ 9.56 (s, 1 H), 8.47 (s, 1 H), 8.08 (d, 1 H), 7.94 (s, 1 H), 7.77 (m, 1 H), 7.62 (m, 2 H), 7.47 (m, 1 H), 7.32 (m, 2 H), 7.24 (d, 1 H) 7.19 (m, 1 H), 5.25 (s, 2 H), 5.19 (t, 1 H), 4.77 (br, I1 H), 3.77 (m, 1 H), 3.66 (m, 1 H), 3.55 (m, 2 H), 2.97 (m, 2 H).

Example 48

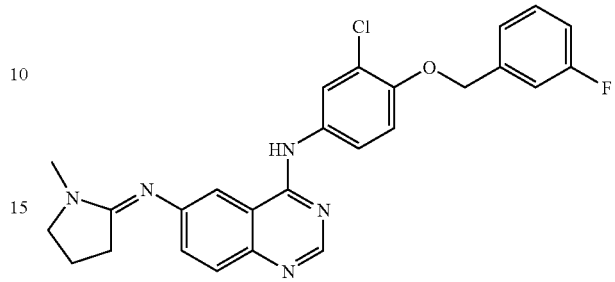

N4-[3-Chloro-4-(3-fluoro-benzyloxy)-phenyl]-N6-(1-methyl-pyrrolidin-2-ylidene)-quinazoline-4,6-diamine N4-[3-Chloro-4-(3-fluoro-benzyloxy)-phenyl]-N6-(1-methyl-pyrrolidin-2-ylidene)-quinazoline-4,6-diamine is prepared by reacting N4-[3-Chloro-4-(3-fluoro-benzyloxy)-phenyl]-quinazoline-4,6-diamine and 1-methyl-pyrrolidin-2-one. Phosphorous oxychloride (0.047 g, 0.30 mmol) is added to a stirred solution of 1-methyl-pyrrolidin-2-one (0.63 g, 0.63 mmol) in methylene chloride (3 ml) at −78° C. under N$_2$ (Bullock et al WO0220526). After 10 minutes, the reaction mixture is warmed to room temperature and stirred for 1 hour. N4-[3-Chloro-4-(3-fluoro-benzyloxy)-phenyl]-quinazoline-4,6-diamine (0.100 g, 0.253 mmol) is added followed by Et$_3$N (0.031 g, 0.30 mmol). After 16 hours, the reaction mixture is quenched with saturated aqueous Na$_2$CO$_3$, the layers separated and the aqueous layer extracted with methylene chloride. The combined organic extracts are dried (Na$_2$SO$_4$), concentrated and purified on a silica gel column (10:2:1 EtOAc: hexanes:MeOH with 0.3% NH$_4$OH solution) to yield 0.010 g (8%) N4-[3-chloro-4-(3-fluoro-benzyloxy)-phenyl]-N6-(1-methyl-pyrrolidin-2-ylidene)-quinazoline-4,6-diamine. MS APCI (+) m/z 476, 478 (M+1, Cl pattern) detected; $^1$H NMR (400 MHz, MeOH4) δ 8.42 (s, 1 H), 7.89 (s, 2 H), 7.77 (d, 1 H), 7.58 (m, 2 H), 7.33 (m, 3 H), 7.18 (d, 1 H), 7.04 (t, 1 H), 5.20 (s, 2 H), 3.60 (t, 2 H), 2.61 (t, 2 H), 2.03 (m, 2 H).

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups.

We claim:
1. A compound having a structure of Formula I:

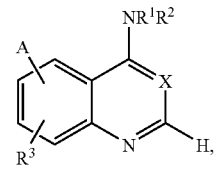

or resolved enantiomers, diastereomers or pharmaceutically acceptable salts thereof; wherein an A group is bonded to at least one of the carbons at the 5, 6, 7 or 8 position of the bicyclic ring, and the ring is substituted by up to three independent $R^3$ groups;

X is N;

$R^1$ is a substituted or unsubstituted phenyl;

$R^2$ is H or a substituted or unsubstituted $C_{1-8}$ alkyl;

$R^3$ is hydrogen, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, —OC(O)$R^6$, —NR$^4$R$^6$, or —OR$^6$, where each of the above alkyl, alkenyl, alkynyl, cycloalkyl and aryl portion of $R^3$ is optionally substituted with one to five groups independently selected from oxo, —OC(O)$R^6$, —NR$^4$R$^6$, —OR$^6$, aryl and arylalkyl, A is —(U)$_n$Z, where n is 0;

Z is

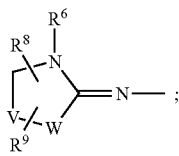

where W and V are selected independently from CR$^7$R$^8$, CR$^8$R$^9$, O, S, SO, SO$_2$, provided if W is O, S, SO, SO$_2$, then V is CR$^8$R$^9$, and provided that $R^6$ directly bonded to Z is not H;

Z includes one or more $R^8$ or $R^9$ groups, wherein said $R^8$ and $R^9$ groups may be bonded to the same or different atoms;

$R^4$ is H or $C_{1-6}$ alkyl;

$R^5$ is trifluoromethyl, $C_1$-$C_{10}$ alkyl, $C_3$-$C_{10}$ cycloalkyl, aryl, arylalkyl, heteroaryl, heteroarylalkyl, heterocyclyl, heterocyclylalkyl, where each alkyl, cycloalkyl, aryl, heteroaryl, heterocyclyl and heterocyclylalkyl is optionally substituted with one to five groups independently selected from oxo, halogen, cyano, nitro, OR$^6$, NR$^4$R$^6$, trifluoromethyl, difluoromethoxy, trifluoromethoxy, azido, aryl, heteroaryl, arylalkyl, heteroarylalkyl, heterocyclyl, and heterocyclylalkyl;

$R^6$, $R^8$ and $R^9$ are independently selected from hydrogen, trifluoromethyl, $C_1$-$C_{10}$ alkyl, (CH$_2$)$_{0-4}$C$_3$-C$_{10}$ cycloalkyl, aryl, arylalkyl, heteroaryl, heteroarylalkyl, heterocyclyl, heterocyclylalkyl, where each alkyl, cycloalkyl, aryl, heteroaryl and heterocyclyl is optionally substituted with one to five groups independently selected from oxo, halogen, cyano, nitro, OR$^6$, NR$^6$R$^8$, trifluoromethyl, difluoromethoxy, trifluoromethoxy, azido, aryl, heteroaryl, arylalkyl, heteroarylalkyl, heterocyclyl, and heterocyclylalkyl;

$R^7$ is hydrogen, halogen, cyano, nitro, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl, heterocyclylalkyl, —NR$^4$SO$_2$R$^5$—SO$_2$NR$^6$R$^4$, —C(O)R$^6$, —C(O)OR$^6$, —NR$^4$C(O)OR$^5$, —NR$^4$C(O)R$^6$, —C(O)NR$^4$R$^6$, —NR$^4$R$^6$, —NR$^4$C(O)NR$^4$R$^6$, —OR$^6$, —S(O)R$^5$, —SO$_2$R$^5$, where each of the above alkyl, alkenyl, alkynyl, cycloalkyl, aryl, heteroaryl and heterocyclyl portion of $R^3$ is optionally substituted with one to five groups independently selected from oxo, halogen, cyano, nitro, trifluoromethyl, difluoromethoxy, trifluoromethoxy, azido, —NR$^4$SO$_2$R$^5$, —SO$_2$NR$^6$R$^4$, —C(O)R$^6$, —C(O)OR$^6$, —OC(O)R$^6$, —NR$^4$C(O)OR$^5$, —NR$^4$C(O)CR$^6$, —C(O)NR$^4$R$^6$, —NR$^4$R$^6$, —NR$^4$C(O)NR$^4$R$^6$, —NR$^4$C(NCN)NR$^4$R$^6$, —OR$^6$, —S(O)R$^5$, —SO$_2$R$^5$, aryl, arylalkyl, heteroaryl, heteroarylalkyl, heterocyclyl, and heterocyclylalkyl;

an $R^4$ group and an $R^6$ group may be independently joined to complete a 3 to 10 membered cyclic ring optionally containing additional heteroatoms selected from the group consisting of O, S, SO, SO$_2$ and NR$^6$ where each ring carbon may be optionally substituted with one to three groups independently selected from halogen, cyano, nitro, trifluoromethyl, difluoromethoxy, trifluoromethoxy, azido, aryl, OR$^8$, NR$^6$R$^8$, heteroaryl, arylalkyl, heteroarylalkyl, heterocyclyl, and heterocyclylalkyl; provided said ring does not contain two adjacent O or two adjacent S atoms;

an $R^6$ group and an $R^8$ group may be independently joined to complete a 3 to 10 membered cyclic ring optionally containing additional heteroatoms selected from the group consisting of O, S, SO, SO$_2$ and NR$^6$ where each ring carbon may be optionally substituted with one to three groups independently selected from halogen, cyano, nitro, trifluoromethyl, difluoromethoxy, trifluoromethoxy, azido, aryl, OR$^8$, NR$^6$R$^8$, heteroaryl, arylalkyl, heteroarylalkyl, heterocyclyl, and heterocyclylalkyl; provided said ring does not contain two adjacent O or two adjacent S atoms;

an $R^7$ group and an $R^8$ group may be independently joined to complete a 3 to 10 membered cyclic ring optionally containing additional heteroatoms selected from the group consisting of O, S, SO, SO$_2$ and NR$^6$ where each ring carbon may be optionally substituted with one to three groups independently selected from halogen, cyano, nitro, trifluoromethyl, difluoromethoxy, trifluoromethoxy, azido, aryl, OR$^8$, NR$^6$R$^8$, heteroaryl, arylalkyl, heteroarylalkyl, heterocyclyl, and heterocyclylalkyl; provided said ring does not contain two adjacent O or two adjacent S atoms; and an $R^8$ group and an $R^9$ group may be independently joined to complete a 3 to 10 membered cyclic ring optionally containing additional heteroatoms selected from the group consisting of O, S, SO, SO$_2$ and NR$^6$ where each ring carbon may be optionally substituted with one to three groups independently selected from halogen, cyano, nitro, trifluoromethyl, difluoromethoxy, trifluoromethoxy, azido, aryl, OR$^8$, NR$^6$R$^8$, heteroaryl, arylalkyl, heteroarylalkyl, heterocyclyl, and heterocyclylalkyl; provided said ring does not contain two adjacent O or two adjacent S atoms.

2. The compound of claim 1, wherein the A group is bonded to at least one of the carbons at the 6 or 7 position of the bicyclic ring.

3. The compound of claim 1, wherein $R^3$ is hydrogen, or OR$^6$.

4. The compound of claim 2, wherein $R^3$ is hydrogen or OR$^6$.

5. The compound of claim 1, wherein $R^2$ is hydrogen,.

6. The compound of claim 1, wherein Z is

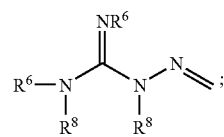

and W is O.

7. The compound of claim 4, wherein Z is

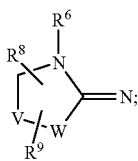

and W is O.

8. The compound of claim 1, wherein the R⁴ group and the R⁶ group are independently joined to complete a 3 to 10 membered cyclic ring optionally containing additional heteroatoms selected from the group consisting of O, S, SO, SO$_2$ and NR⁶ where each ring carbon may be optionally substituted with one to three groups independently selected from halogen, cyano, nitro, trifluoromethyl, difluoromethoxy, trifluoromethoxy, azido, aryl, OR⁸, NR⁶R⁸, heteroaryl, arylalkyl, heteroarylalkyl, heterocyclyl, and heterocyclylalkyl; provided said ring does not contain two adjacent O or two adjacent S atoms.

9. The compound of claim 1, wherein the R⁶ group and the R⁸ group are independently joined to complete a 3 to 10 membered cyclic ring optionally containing additional heteroatoms selected from the group consisting of O, S, SO, SO$_2$ and NR⁶ where each ring carbon may be optionally substituted with one to three groups independently selected from halogen, cyano, nitro, trifluoromethyl, difluoromethoxy, trifluoromethoxy, azido, aryl, OR⁸, NR⁶R⁸, heteroaryl, arylalkyl, heteroarylalkyl, heterocyclyl, and heterocyclylalkyl; provided said ring does not contain two adjacent O or two adjacent S atoms.

10. The compound of claim 1, wherein the R⁷ group and the R⁵ group are independently joined to complete a 3 to 10 membered cyclic ring optionally containing additional heteroatoms selected from the group consisting of O, S, SO, SO$_2$ and NR⁶ where each ring carbon may be optionally substituted with one to three groups independently selected from halogen, cyano, nitro, trifluoromethyl, difluoromethoxy, trifluoromethoxy, azido, aryl, OR⁸, NR⁶R⁸, heteroaryl, arylalkyl, heteroarylalkyl, heterocyclyl, and heterocyclylalkyl; provided said ring does not contain two adjacent O or two adjacent S atoms.

11. The compound of claim 1, wherein the R⁸ group and the R⁹ group are independently joined to complete a 3 to 10 membered cyclic ring optionally containing additional heteroatoms selected from the group consisting of O, S, SO, SO$_2$ and NR⁶ where each ring carbon may be optionally substituted with one to three groups independently selected from halogen, cyano, nitro, trifluoromethyl, difluoromethoxy, tritluoromethoxy, azido, aryl, OR⁸, NR⁶R⁸, heteroaryl, arylalkyl, heteroarylalkyl, heterocyclyl, and heterocyclylalkyl; provided said ring does not contain two adjacent O or two adjacent S atoms.

12. A method of treating cancer of the colon, ovary, bladder, breast, Stomach esophagus, lung, uterus and prostate in a mammal comprising administering a therapeutically effective amount of the compound defined in claim 1 to said mammal.

13. A method of treating cancer of the colon, ovary, bladder, breast, stomach, esophagus, lung, uterus and prostate in a mammal comprising administering a therapeutically effective amount of the compound defined in claim 2 to said mammal.

14. A method of treating cancer of the colon, ovary, bladder, breast, stomach, esophagus, lung, uterus and prostate in a mammal comprising administering a therapeutically effective amount of the compound defined in claim 3 to said mammal 15. A method of treating cancer of the colon, ovary, bladder, breast, stomach, esophagus, lung, uterus and prostate in a mammal comprising administering a therapeutically effective amount of the compound defined in claim 4 to said mammal.

16. A method of treating cancer of the colon, ovary, bladder, breast, stomach, esophagus, lung, uterus and prostate in a mammal comprising administering a therapeutically effective amount of the compound defined in claim 5 to said mammal.

17. A method of treating cancer of the colon, ovary, bladder, breast, stomach, esophagus, uterus and prostate in a mammal comprising administering a therapeutically effective amount of the compound defined in claim 6 to said mammal.

18. A method of treating cancer of the colon, ovary, bladder, breast, stomach, esophagus, lung, uterus and prostate in a mammal comprising administering a therapeutically effective amount of the compound defined in claim 7 to said mammal.

19. A method of treating cancer of the colon, ovary, bladder, breast stomach, esophagus, lung, uterus and prostate in a mammal comprising administering a therapeutically effective amount of the compound defined in claim 8 to said mammal.

20. A method of treating cancer of the colon, ovary, bladder, breast, stomach, Esophagus, lung, uterus and prostate in a mammal comprising administering a therapeutically effective amount of the compound defined in claim 9 to said mammal.

21. A method of treating cancer of the colon. ovary, bladder, breast, stomach, esophagus, lung, uterus and prostate in a mammal comprising administering a therapeutically effective amount of the compound defined in claim 10 to said mammal.

22. A method of treating cancer of the colon, ovary, bladder, breast, stomach, esophagus, lung, uterus and prostate in a mammal comprising administering a therapeutically effective amount of the compound defined in claim 11 to said mammal.

23. The compound of claim 1, wherein R¹ is selected from the structures:

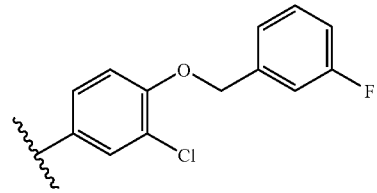

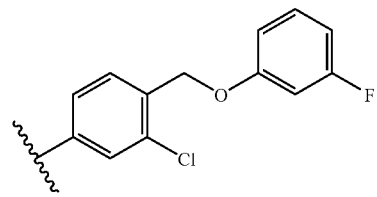

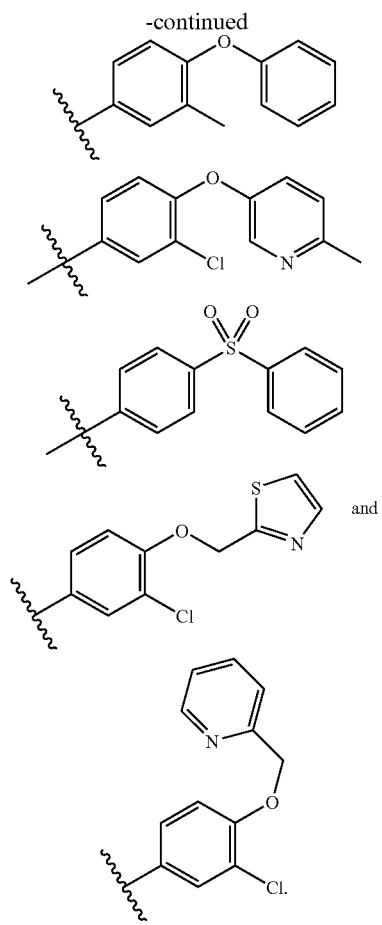

24. The compound of claim 6, wherein $R^6$ is an optionally substituted alkyl or cycloalkyl.

25. The compound of claim 24, wherein $R^6$ is methyl, ethyl, $CH_2CF_3$, $CH_2CH_2OH$, or cyclopropyl.

26. The compound of claim 24, wherein $R^8$ and $R^9$ are independently an optionally substituted alkyl.

27. The compound of claim 26, wherein $R^8$ and $R^9$ are independently $CH_2OH$, $CH_2NMe_2$ or $CH_2O$-t-butyl.

28. The compound of claim 24, wherein $R^8$ and $R^9$ together with the atoms to which they are attached form an optionally substituted heterocyclic ring.

29. The compound of claim 6, wherein Z is selected from the structures:

30. The compound of claim 1, wherein Z is

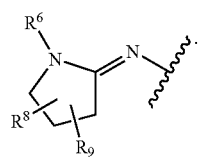

31. The compound of claim 30, wherein $R^6$ is an optionally substituted alkyl.

32. The compound of claim 31, wherein $R^6$ is methyl.

33. The compound of claim 32, wherein Z is

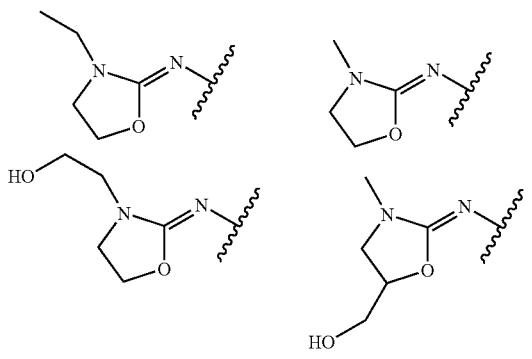

34. The compound of claim 1, selected from:
N4-[3-Chloro-4-(3-fluorobenzyloxy)-phenyl]-N6-(3-methyl-oxazolidin-2-ylidene)-quinazoline-4,6-diamine;
N-4-[3-Chloro-4-(3-fluorobenzyloxy)-phenyl]-N6-(3-ethyl-oxazolidin-2-ylidene)-quinazoline-4,6-diamine;
(2-{4-[3-Chloro-4-(3-fluorobenzyloxy)-phenylamino]-quinazolin- 6-ylimino}-3-methyl-oxazolidin-5-yl)-methanol;

2-(2-{4-[3-Chloro-4-(3-fluorobenzyloxy)-phenylamino]-quinazolin-6-ylimino}-oxazolidin-3-yl)-ethanol;

N-4-[3-Chloro-4-(3-fluorobenzyloxy)-phenyl]-N6-(4-dimethylaminomethyl-3-methyl-oxazolidin-2-ylidene)-quinazoline-4,6-diamine;

(S)-N6-(4-tert-Butoxymethyl-3-methyl-oxazolidin-2-ylidene)-N4-[3-chloro-4-(3-fluoro-phenoxymethyl)-phenyl]-quinazoline-4,6-diamine;

(S)-(2-{4-[3-Chloro-4-(3-fluorophenoxymethyl)-phenylamino]-quinazolin-6-ylimino}-3-methyl-oxazolidin-4-yl)-methanol;

(2-{4-[3-Chloro-4-(3-fluorophenoxymethyl)-phenylamino]-quinazolin-6-ylimino}-3-methyl-oxazolidin-5-yl)-methanol;

{3-Methyl-2-[4-(3-methyl-4-phenoxyphenylamino)-quinazolin-6-ylimino]-oxazolidin-5-yl}-methanol;

(2-{4-[3-Chloro-4-(6-methylpyridin-3-yloxy)-phenylanino]-quinazolin-6-ylimino}-3-methyl-oxazolidin-5-yl)-methanol;

N4-(4-Benzenesulfonylphenyl)-N6-(3-methyloxazolidin-2-ylidene)-quinazoline-4,6-diamine;

{2-[4-(4-Benzenesulfonylphenylamino)-quinazolin-6-ylimino]-3-methyl-oxazolidin-5-yl}-methanol;

N4-(4-Benzenesulfonylphenyl)-N6-(3-cyclopropyloxazolidin-2-ylidene)-quinazoline-4,6-diamine;

N6-(Diniethylhexahydropyrrolo[3,4-d]oxazol-2-ylidene)-N4-(3-methyl4-phenoxyphenyl)-quinazoline-4,6-diamine;

N4-[3-Chloro-4-(thiazol-2-ylmethoxy)-phenyl]-N6-(3-methyloxazolidin-2-ylidene)-quinazoline-4,6-diamine;

N4-[3-Chloro-4-(pyridin-2-ylmethoxy)-phenyl]-N6-(dimethyl-3-oxa-1 ,8-diaza-spiro[4.5]dec-2-ylidene)-quinazoline-4,6-diamine;

[2-{4-[3-Chloro-4-(3-fluorobenzyloxy)-phenylamino]-quinazolin-6-ylimino}-3-(2,2,2-trifluoroethyl)-oxazolidin-5-yl]-methanol; and N4-[3-Chloro-4-(3-fluorobenzyloxy)-phenyl]-N6-(1-methylpyrrolidin-2-ylidene)-quinazoline-4,6-diamine.

35. A compound having a structure of Formula I:

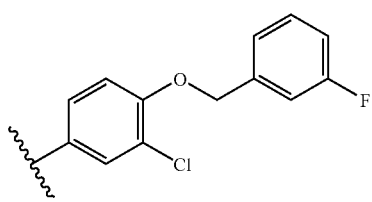
(I)

or resolved enantiomers, diastereomers or pharmaceutically acceptable salts thereof, wherein X is N;

$R^1$ is selected from the structures:

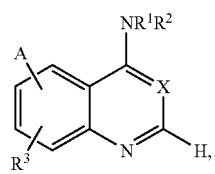

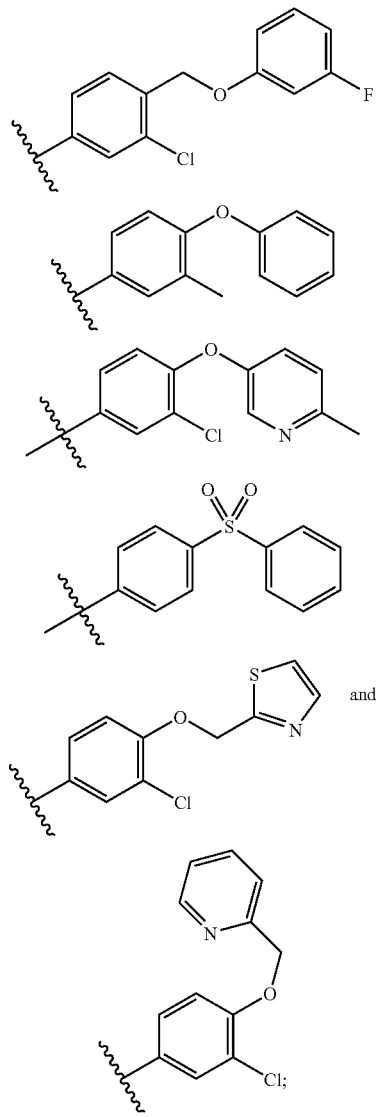

-continued and $R^2$ is hydrogen or a substituted or unsubstituted $C_{1-8}$ alkyl;

$R^3$ is hydrogen, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, —OC(O)$R^6$, —NR$^4$R$^6$, or —OR$^6$, where each of the above alkyl, alkenyl, alkynyl, cycloalkyl and aryl portion of $R^3$ is optionally substituted with one to five groups independently selected from oxo, —OC(O)$R^6$, —NR$^4$R$^6$, —OR$^6$, aryl and arylalkyl;

A is —(U)$_n$Z, where n is 0; and

Z is selected from the following structures:

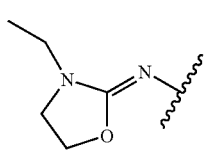 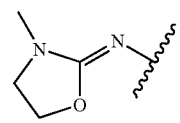

-continued
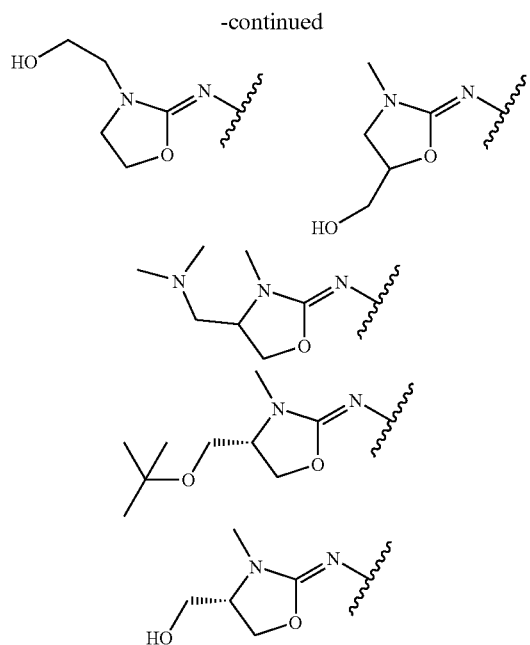
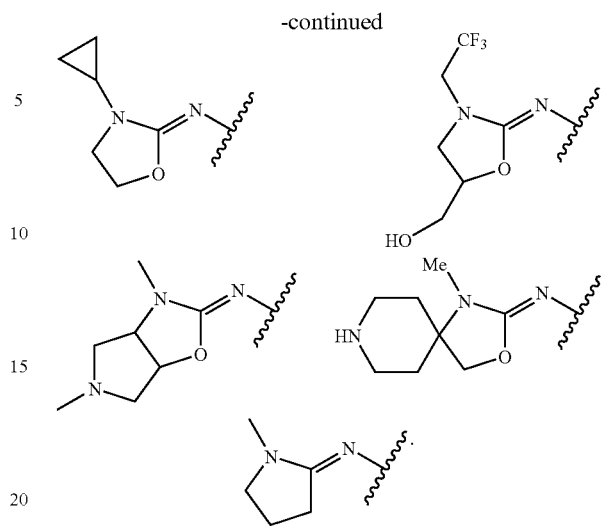
36. The compound of claim 35, wherein $R^2$ is hydrogen.
37. The compound of claim 35, wherein $R^3$ is hydrogen.
* * * * *